US008590766B2

(12) United States Patent
Okauchi et al.

(10) Patent No.: US 8,590,766 B2
(45) Date of Patent: *Nov. 26, 2013

(54) METHOD AND APPARATUS FOR INSPECTING JOINED OBJECT FORMED BY FRICTION STIR JOINING

(75) Inventors: Hironori Okauchi, Kobe (JP); Mamoru Nishio, Kobe (JP); Hideyuki Hirasawa, Kobe (JP)

(73) Assignee: Kawasaki Jukogyo Kabushiki Kaisha, Kobe-Shi (JP)

( * ) Notice: Subject to any disclaimer, the term of this patent is extended or adjusted under 35 U.S.C. 154(b) by 194 days.

This patent is subject to a terminal disclaimer.

(21) Appl. No.: 12/926,524

(22) Filed: Nov. 23, 2010

(65) Prior Publication Data

US 2011/0100525 A1 May 5, 2011

Related U.S. Application Data

(63) Continuation of application No. 12/226,206, filed as application No. PCT/JP2007/055496 on Mar. 19, 2007, now Pat. No. 7,861,910.

(30) Foreign Application Priority Data

Apr. 11, 2006 (JP) ................................. 2006-109071

(51) Int. Cl.
*B23K 20/12* (2006.01)
*B23K 31/12* (2006.01)

(52) U.S. Cl.
USPC .......................... 228/104; 228/2.1; 228/112.1

(58) Field of Classification Search
None
See application file for complete search history.

(56) References Cited

U.S. PATENT DOCUMENTS

| 3,575,044 A | 4/1971 | Gibbs et al. |
| 3,868,847 A | 3/1975 | Gunkel |

(Continued)

FOREIGN PATENT DOCUMENTS

| JP | A-56-035057 | 4/1981 |
| JP | A-03-233352 | 10/1991 |

(Continued)

OTHER PUBLICATIONS

Wu, "Nonlinear Interaction of Ultrasound with an Unbounded Rough Interface", *2005 IEEE Ultrasonics Symposium*, vol. 1, 2005, pp. 289-292.

(Continued)

*Primary Examiner* — Kiley Stoner
(74) *Attorney, Agent, or Firm* — Oliff & Berridge, PLC

(57) ABSTRACT

This invention provides a method for inspecting a joined region and joining strength of a joined object formed by a spot friction stir joining process. In this method, an ultrasonic wave is introduced into the joined object from a backing face 25 opposed to a joining tool plunging face 24 and the ultrasonic wave reflected from the joined object 20 is taken in. In this case, the joining region 21 and the joining strength is estimated by observing a reflected wave of the ultrasonic wave in the vicinity of a position, along a reference direction Z, corresponding to an interface 27 of two joining members, without using the reflected wave of the ultrasonic wave reflected from the joining tool plunging face, thereby inspecting the joined object based on the estimation result. Thus, influence of a concave/convex shape of a joining mark 29 formed in the joining tool plunging face 24 can be avoided, and the use of the ultrasonic wave for estimating the joined region 21 can achieve an inspection of joining quality without destroying the joined object 20.

4 Claims, 21 Drawing Sheets

(56) References Cited

U.S. PATENT DOCUMENTS

| | | | |
|---|---|---|---|
| 4,487,070 A | 12/1984 | Gerling et al. | |
| 4,554,128 A | 11/1985 | Parker et al. | |
| 4,606,490 A | 8/1986 | Chan et al. | |
| 4,712,722 A | 12/1987 | Hood et al. | |
| 4,785,667 A | 11/1988 | Miyajima et al. | |
| 5,085,082 A | 2/1992 | Cantor et al. | |
| 5,474,225 A | 12/1995 | Geier et al. | |
| 5,537,876 A | 7/1996 | Davidson et al. | |
| 5,677,490 A | 10/1997 | Gunther et al. | |
| 5,777,229 A | 7/1998 | Geier et al. | |
| 6,072,144 A * | 6/2000 | Perryman | 219/109 |
| 6,155,117 A | 12/2000 | Stevens et al. | |
| 6,273,320 B1 | 8/2001 | Siebert et al. | |
| 6,302,314 B1 | 10/2001 | Horio et al. | |
| 6,365,873 B1 | 4/2002 | Smartt et al. | |
| 6,450,392 B1 | 9/2002 | Nakamura et al. | |
| 6,460,752 B1 | 10/2002 | Waldron et al. | |
| 6,530,278 B1 | 3/2003 | Bowersox et al. | |
| 6,546,803 B1 * | 4/2003 | Ptchelintsev et al. | 73/632 |
| 6,595,402 B2 | 7/2003 | Nakamura et al. | |
| 6,896,171 B2 | 5/2005 | Den Boer et al. | |
| 6,948,369 B2 | 9/2005 | Fleming et al. | |
| 7,036,376 B2 | 5/2006 | Arndt | |
| 7,132,617 B2 * | 11/2006 | Lee et al. | 219/109 |
| 7,562,803 B2 * | 7/2009 | Takase et al. | 228/112.1 |
| 2002/0014514 A1 | 2/2002 | Shimizu et al. | |
| 2003/0057258 A1 | 3/2003 | Ishida et al. | |
| 2004/0045358 A1 | 3/2004 | Wagner et al. | |
| 2004/0050907 A1 | 3/2004 | Dracup et al. | |
| 2004/0134970 A1 | 7/2004 | Den Boer et al. | |
| 2004/0245315 A1 | 12/2004 | Maev et al. | |
| 2006/0065698 A1 | 3/2006 | Ishikawa et al. | |
| 2006/0108394 A1 | 5/2006 | Okaniwa et al. | |
| 2006/0265876 A1 | 11/2006 | Kimura et al. | |
| 2007/0234809 A1 | 10/2007 | Klein et al. | |
| 2008/0006678 A1 * | 1/2008 | Packer et al. | 228/114.5 |
| 2008/0135601 A1 * | 6/2008 | Chen et al. | 228/102 |
| 2008/0149687 A1 | 6/2008 | Garnett et al. | |
| 2009/0013516 A1 * | 1/2009 | Waddell et al. | 29/402.09 |
| 2009/0078742 A1 | 3/2009 | Pasquali et al. | |
| 2009/0133500 A1 | 5/2009 | Bui et al. | |
| 2009/0134203 A1 * | 5/2009 | Domec et al. | 228/112.1 |
| 2010/0117636 A1 * | 5/2010 | Dasch | 324/222 |

FOREIGN PATENT DOCUMENTS

| | | |
|---|---|---|
| JP | 2000-146928 A * | 5/2000 |
| JP | A-2000-146928 | 5/2000 |
| JP | A-2004-317475 | 11/2004 |
| WO | WO 2004/112985 A1 | 12/2004 |

OTHER PUBLICATIONS

Mar. 29, 2010 Office Action issued in U.S. Appl. No. 12/226,206.

Welding Handbook, Eighth Edition, vol. 1, 1991, pp. 470, 502 and 505.

Aug. 24, 2010 Notice of Allowance issued in U.S. Appl. No. 12/226,206.

Bird, C.R., "Ultrasonic phased array inspection technology for the evaluation of friction stir welds," *Insight*, Jan. 2004, pp. 31-36, vol. 46, No. 1.

Thomas, Wayne M., "Friction Stir Welding-Recent Developments in Tool and Process Technologies," *Advanced Engineering Materials*, 2003, pp. 485-490, vol. 5, No. 7.

Nov. 4, 2011 Extended European Search Report issued in European Patent Application No. 07738941.9.

* cited by examiner

METHOD AND APPARATUS FOR INSPECTING JOINED OBJECT FORMED BY FRICTION STIR JOINING

CROSS REFERENCE TO RELATED APPLICATIONS

This is a Continuation of application Ser. No. 12/226,206 filed Nov. 7, 2008 now U.S. Pat. No. 7,861,910, which in turn is a National Phase of Application No. PCT/JP2007/055496 filed Mar. 19, 2007. This application is based upon and claims the benefit of priority from the prior Japanese Patent Application No. 2006-109071 filed Apr. 11, 2008. The disclosure of the prior applications is hereby incorporated by reference herein in its entirety.

TECHNICAL FIELD

The present invention relates to a method for inspecting and estimating a joined region and joining strength of an object by means of a non-destructive inspection, the object being formed by joining two members together by using a friction stir joining method.

BACKGROUND ART

FIG. 25 is a diagram for illustrating a method for estimating a welded region 2 of a welded object 1 welded by a conventional resistance spot welding. As shown in FIG. 25, the welded object 1 is formed by spot-welding an upper plate 3 and a lower plate 4 together at the welded region 2. In the welded region 2, the upper plate 3 and the lower plate 4 are welded together due to disappearance of an interfacial portion 5, caused by melting, between the upper plate 3 and the lower plate 4. In non-welded regions 6 except for the welded region 2 of the welded object 1, the interfaces 5 remain between the upper plate 3 and the lower plate 4.

The welded region 2 includes a nugget portion 7, in which the upper plate 3 and the lower plate 4 are melted and welded together, and a corona-bonded portion 8, which covers the nugget portion 7 and in which the upper plate 3 and the lower plate 4 are slightly melted and closely adhered together. In the resistance spot welding, a front face 9 and a rear face 10 of the welded object 1 are arranged to be substantially parallel with each other.

As a conventional art, there is a method for estimating the welded region 2 of the welded object 1 by using an ultrasonic wave. In the conventional art, an ultrasonic probe 11 adapted to generate the ultrasonic wave is scanned to pass through over the welded region 2 so as to take therein a reflected wave of the ultrasonic wave reflected from the welded object 1 for each scanning displacement. The reflected wave 12 of the ultrasonic wave introduced in and reflected from the welded object 1 will be a reflected wave reflected from a bottom face 13 of the upper plate 3 in the non-welded regions 6, while it will be a reflected wave reflected from a bottom face 14 of the lower plate 4 in the welded region 2. In this conventional estimating method, boundary positions 15 between the welded region 2 and the non-welded regions 6 are estimated by comparing the reflected waves from the upper plate 13 and from the lower plate 14, thus estimating a size of the welded region 2.

In a technique disclosed in Patent Document 1, as an estimation of the welded region 2 in the welded object 1, the nugget portion 7 is obtained based on attenuation of multiple reflection waves multiply reflected from a top face 16 of the upper plate 3 and from the bottom face 14 of the lower plate 4. In a technique disclosed in Patent Document 2, as the estimation of the welded region 2 in the welded object 1, the nugget portion 7 is obtained based on a level of a transverse ultrasonic wave generated by mode conversion that is caused when an ultrasonic wave is reflected by the bottom face 14 of the lower plate 4.

As another conventional art, there is a method for estimating a joined region by employing an ultrasonic wave, the joined region being formed by a continuous friction stir joining. In a technique disclosed in Patent Document 3, presence of holes indicative of a defect of joining in the joined region is detected when amplitude of a bottom face echo reflected from a bottom face of a joined object is lower than a theoretical value. It is noted that the joined object formed by the continuous friction stir joining has a substantially flat front face.

Patent Document 1: JP 3-233352 A
Patent Document 2: JP 2000-146928 A
Patent Document 3: JP 2004-317475 A As one of joining methods, there is a lap-joint-joining method utilizing the friction stir joining method. Namely, in a lap joint formed by the friction stir joining method, the upper plate and the lower plate are joined together due to disappearance of the interfacial portion, which was stirred between the upper plate and the lower plate. Conventionally, the joined region and the joining strength of a lap-joint-joined object formed by the friction stir joining method are obtained by a destructive inspection, respectively. Therefore, there still remains a need for a method and an apparatus for obtaining the joined region and the joining strength by a non-destructive inspection also in the case of the lap-joint joined object formed by the friction stir joining method.

However, the joined object formed by the friction stir joining method generally includes a non-flat tool-processing or tool-plunging face having a complex concave/convex shape. Therefore, in the technique of the non-destructive inspection employing the reflected wave reflected from the bottom face 14 of the bottom plate, the reflected wave is affected by such a concave/convex shape of the tool-plunging face. This makes it difficult to obtain the joined region and the joining strength with respect to an object formed by a spot friction stir joining method.

DISCLOSURE OF INVENTION

Therefore, it is an object of the present invention to provide an estimation method and an estimation apparatus for estimating the joined region and/or joining strength of the joined object formed by the spot friction stir joining method.

It is another object of the present invention to provide a method and an apparatus for inspecting the joined region and/or joining strength of the object formed by the spot friction stir joining method, without performing a destructive inspection.

The present invention is a method of estimating a joined region of a joined object in which two joining members are joined together while being overlapped one on another by using a friction stir joining method, comprising:

a reflected wave measuring step of introducing an ultrasonic wave into the joined object from a face of the joined object opposed to an plunging face thereof in which a joining tool was plunged upon a friction stir process, and taking in a reflected wave of the ultrasonic wave introduced into and reflected from the joined object; and an estimation step of estimating an ultrasonic wave incident position as a position over the joined region, provided that among reflected waves taken in by the reflected wave measuring step, an observed reflected wave reflected in a vicinity of a position corresponding to an interface between the two joining members satisfies a predetermined boundary condition.

According to this invention, in the reflected wave measuring step, the ultrasonic wave is introduced into the joined object from the face opposed to the plunging face in which the joining tool was plunged, while the ultrasonic wave reflected from the joined object is taken in. In a non-joined region, because an interface between one joining member and the other joining member does not completely disappear, the ultrasonic wave introduced from the one joining member is reflected from the interface between the one joining member and the other joining member. On the other hand, in the joined region, because the one joining member and the other joining member are joined together and the interface therebetween has been disappeared, the ultrasonic wave introduced from the one joining member is transmitted into the other joining member without being reflected by the one joining member, as such the reflected wave reflected in the vicinity of a position corresponding to the interface between the two joining members will be quite reduced or substantially lost.

Accordingly, a feature or features of the observed reflected wave will change between the case in which the ultrasonic wave incident position is located over the non-joined region and the case in which the same incident position is located over the joined region. By judging whether or not the observed reflected wave satisfies the predetermined boundary condition, based on changing amounts of the feature's value of the observed reflected wave, it can be estimated which of the non-joined region or joined region the ultrasonic wave incident position is located over.

In this invention, the ultrasonic wave is introduced into the joined object from the face opposed to the plunging face in which the joining tool was plunged. Consequently, the ultrasonic wave can be introduced into the joined object without being affected by the concave/convex shape formed in the tool plunging face. This can also prevent the ultrasonic probe from contacting with a tool plunging mark of the joined object, thereby avoiding damage of the ultrasonic probe. In this invention, in the estimation step, the joined region is estimated by observing the reflected wave of the ultrasonic wave reflected in the vicinity of the position corresponding to the interface of the two joining members, without utilizing the reflected wave of the ultrasonic wave reflected from the joining tool plunging face. Thus, the joined region can be estimated without being affected by the concave/convex shape of the joining tool plunging face.

In this way, by estimating the joined region by using the ultrasonic wave, the quality of joining can be estimated without destroying the joined object. Thus, the cost required for the quality inspection can be reduced as compared with the case requiring the destructive inspection. Even in the case of a large-size joined object for which the destructive inspection is generally difficult, the joining quality can be estimated with ease.

In the present invention, in the reflected wave measuring step, the ultrasonic wave incident position is scanned so as to pass through over the joined region, while the reflected wave of the ultrasonic wave introduced into the joined object is taken in for each displacement of scanning position.

According to this invention, by scanning the ultrasonic wave incident position so as to pass through over the joined region, the position over the boundary between the joined region and the non-joined region, which would be located on the straight line along the scanning direction, can be estimated, thereby estimating a general size of the joined region. Consequently, the joining strength can be obtained as well as information necessary for works for inspecting the joining quality or the like can be provided.

In the present invention, the boundary condition is set based on the reflected wave reflected at the interface of the two joining members when the ultrasonic wave incident position is located over a non-joined region.

According to this invention, the boundary condition is set based on the observed reflected wave in the case in which the ultrasonic wave incident position is located over the non-joined region. Thus, the boundary condition can be set for each joined object, and therefore the joined region can be precisely estimated even in the case in which there are variations of the boundary condition for each joined object.

In the present invention, in the estimation step, the ultrasonic wave incident position, in which an amplitude of the observed reflected wave is lower than a predetermined amplitude threshold value, is estimated as the position over the joined region.

According to this invention, when the ultrasonic wave incident position is located over the joined region, the ultrasonic wave introduced into the joined object is transmitted from the one joining member into the other joining member. Therefore, the amplitude of the ultrasonic wave reflected from the position corresponding to the interface of the two joining members will be relatively low. Accordingly, the ultrasonic wave incident position, in which the amplitude of the observed reflected wave is lower than the predetermined amplitude threshold value, can be estimated as the position over the joined region. Since this estimation is based on the amplitude of the observed reflected wave, there is no need for analyzing frequencies of wave forms included in the reflected wave, as such facilitating the estimation of the joined region.

In the present invention, in the estimation step, the ultrasonic wave incident position, in which a central frequency that is a center of a frequency distribution band of a wave form higher than an amplitude value lower by a predetermined amount than a maximum amplitude value in the frequency distribution band of the wave form included in the observed reflected wave is lower than a predetermined frequency threshold value, is estimated as the position over the joined region.

According to this invention, in the case in which the ultrasonic wave incident position is located over the joined region, the ultrasonic wave is more likely to be transmitted from the one joining member into the other joining member, as compared with the case in which the ultrasonic wave incident position is located over the non-joined region. Among the wave forms included in the reflected wave, the wave forms in a higher frequency band will exhibit higher directivity as compared with the wave forms in a lower frequency band. If the boundary face between the joined region and the remaining region not subjected to the friction stir process is inclined relative to the ultrasonic wave incident face on the side of the ultrasonic wave incident face, the wave forms in the higher frequency band will be taken in, in a lesser amount, as the reflected wave. Besides, the wave forms in the higher frequency band are more likely to be lowered as compared with those in the lower frequency band. In view of this point, in the case in which the ultrasonic wave incident position is located over the joined region, the central frequency of the observed reflected wave is lowered, as compared with the case in which the same incident position is located over the non-joined region.

Accordingly, the ultrasonic wave incident position, in which the central frequency of the observed reflected wave is lower than the predetermined frequency threshold value, can be estimated as the position over the joined region. With the frequency analysis, the joined region can be precisely estimated even in the case in which the echo level is significantly lower as well as in the case in which considerable noise is generated. For instance, the predetermined frequency threshold value is set lower than the central frequency of the observed reflected wave in the case in which the ultrasonic wave incident position is located over the non-joined region.

In the present invention, in the estimation step, the ultrasonic wave incident position, in which a peak frequency that is a frequency of a wave form exhibiting a maximum amplitude value in a frequency distribution band of the wave form included in the observed reflected wave is lower than a predetermined frequency threshold value, is estimated as the position over the joined region.

According to this invention, in the case in which the ultrasonic wave incident position is located over the joined region, the ultrasonic wave is more likely to be transmitted from the one joining region into the other joining region, as compared with the case in which the same incident position is located over the non-joined region. Among the wave forms included in the reflected wave, the higher frequency wave forms will exhibit higher directivity as compared with the lower frequency wave forms. If the boundary face between the joined region and the remaining region not subjected to the friction stir process is inclined relative to the ultrasonic wave incident face on the side of the ultrasonic wave incident face, the higher frequency wave forms will be taken in, in a lesser amount, as the reflected wave. Besides, the higher frequency wave forms are more likely to be lowered as compared with the lower frequency wave forms. In view of this point, in the case in which the ultrasonic wave incident position is located over the joined region, the peak frequency of the observed reflected wave is lowered, as compared with the case in which the same incident position is located over the non-joined region.

Accordingly, the ultrasonic wave incident position, in which the peak frequency of the observed reflected wave is lower than the predetermined frequency threshold value, can be estimated as the position over the joined region. With the frequency analysis, the joined region can be precisely estimated even in the case in which the echo level is significantly lower as well as in the case in which considerable noise is generated. For instance, the predetermined frequency is set lower than the central frequency of the observed reflected wave in the case in which the ultrasonic wave incident position is located over the non-joined region. In addition, due to the estimation of the joined region based on the peak frequency, the joined region can be estimated, even in the case in which the frequency distribution of each wave form included in the observed reflected wave is shifted to some extent from a normal distribution.

In the present invention, in the estimation step, the ultrasonic wave incident position, in which a frequency distribution bandwidth of a wave form greater than an amplitude value lower by a predetermined amount than a maximum amplitude value in a frequency distribution band of the wave form included in the observed reflected wave is greater than a predetermined frequency bandwidth threshold value, is estimated as the position over the joined region.

According to this invention, in the case in which the ultrasonic wave incident position is located over the joined region, the ultrasonic wave is more likely to be transmitted from the one joining region into the other joining region, as compared with the case in which the same incident position is located over the non-joined region. Among the wave forms included in the reflected wave, the higher frequency wave forms will exhibit higher directivity as compared with the lower frequency wave forms. If the boundary face between the joined region and the remaining region not subjected to the friction stir process is inclined relative to the ultrasonic wave incident face on the side of the ultrasonic wave incident face, the higher frequency wave forms will be taken in, in a lesser amount, as the reflected wave. Besides, the higher frequency wave forms are more likely to be lowered as compared with the lower frequency wave forms. In view of this point, in the case in which the ultrasonic wave incident position is located over the joined region, dispersion of the frequency distribution of the wave form included in the observed reflected wave becomes greater as compared with the case in which the same incident position is located over the non-joined region, as such further widening the frequency distribution bandwidth of the wave form greater than the amplitude value which is lowered by the predetermined amount from the maximum amplitude value.

Accordingly, the ultrasonic wave incident position, in which the frequency distribution bandwidth of the observed reflected wave is greater than the predetermined frequency bandwidth threshold value, can be estimated as the position over the joined region. For instance, the predetermined frequency bandwidth threshold value is set wider than the frequency bandwidth in the case in which the ultrasonic wave incident position is located over the non-joined region. With the frequency analysis, the joined region can be precisely estimated even in the case in which the echo level is significantly lower as well as in the case in which considerable noise is generated. In addition, due to the estimation of the joined region based on the peak frequency, the joined region can be estimated adequately, even in the case in which the frequency distribution of each wave form included in the observed reflected wave is shifted to some extent from a normal distribution.

The present invention is a method of estimating a joining strength of a joined object in which two joining members are joined together while being overlapped one on another by using a friction stir joining method, comprising:

a reflected wave measuring step of introducing an ultrasonic wave into the joined object from a face of the joined object opposed to an plunging face thereof in which a joining tool was plunged upon a friction stir process, and taking in a reflected wave of the ultrasonic wave introduced into and reflected from the joined object;

a joined region estimation step of, estimating an ultrasonic wave incident position as a position over the joined region, provided that among reflected waves taken in by the reflected wave measuring step, an observed reflected wave reflected in a vicinity of a position corresponding to an interface between the two joining members satisfies a predetermined boundary condition; and a strength estimation step of estimating a size of the joined region based on the position over the joined region estimated in the joined region estimation step and estimating the joining strength of the joined object based on an estimated size of the joined region.

According to this invention, in the reflected wave measuring step, the ultrasonic wave is introduced into the joined object from the face opposed to the plunging face in which the joining tool was plunged, while the reflected wave of the ultrasonic wave reflected from the joined object is taken in. A feature or features of the observed reflected wave will change between the case in which the ultrasonic wave incident position is located over the non-joined region and the case in which the same incident position is located over the joined region. By judging whether or not the observed reflected wave satisfies the predetermined boundary condition, based on the feature's value of the observed reflected wave, it can be estimated which of the non-joined region or joined region the ultrasonic wave incident position is located over.

In this invention, the ultrasonic wave is introduced into the joined object from the face opposed to the plunging face in which the joining tool was plunged. Consequently, the ultrasonic wave can be introduced into the joined object without being affected by the concave/convex shape formed in the tool plunging face. This can also prevent the ultrasonic probe from contacting with the tool plunging mark of the joined object, thereby avoiding damage of the ultrasonic probe. In this invention, in the joined region estimation step, the joined region is estimated by observing the reflected wave of the ultrasonic wave reflected in the vicinity of the position corresponding to the interface of the two joining members, without utilizing the reflected wave of the ultrasonic wave reflected from the joining tool plunging face. Thus, the joined region can be estimated, without being affected by the concave/convex shape of the joining tool plunging face, by estimating the joined region without utilizing the reflected wave of the ultrasonic wave reflected by the joining tool plunging face.

In the strength estimating step, the size of the joined region is estimated, based on the estimation result obtained by the joined region estimation step. The size of the joined region and the joining strength is in a generally one-to-one relation. Accordingly, based on the size of the joined region, the joining strength of the joined object can be estimated.

In this manner, by estimating the joining strength of the joined object by using the ultrasonic wave, the joining strength can be estimated without destroying the joined object, as such reducing the cost required for the quality inspection as compared with the case requiring the destructive inspection. Additionally, even in the case of a large-size joined object for which the destructive inspection is usually difficult, the joining strength can be estimated.

The present invention is a method of estimating a joining strength of a joined object in which two joining members are joined together while being overlapped one on another by using a friction stir joining method, comprising:

a reflected wave measuring step of introducing an ultrasonic wave into the joined object from a face of the joined object opposed to an plunging face thereof in which a joining tool was plunged upon a friction stir process, and taking in a reflected wave of the ultrasonic wave introduced into and reflected from the joined object, for a unit range including a region over a joined region of the joined object; and a strength estimation step of estimating the joining strength of the joined object, based on an integrated feature's value of an observed reflected wave reflected in a vicinity of a position corresponding to an interface of the two joining members, among reflected waves taken in by the reflected wave measuring step, for the unit range, as well as on a relation of conversion which is set for converting the integrated feature's value into a strength of the joined object.

According to this invention, in the reflected wave measuring step, the ultrasonic wave is introduced into the joined object from the face opposed to the plunging face in which the joining tool was plunged, while the ultrasonic wave reflected from the joined object is taken in. The integrated feature's value of the observed reflected wave in the unit range including a region over the joined region is changed, depending on the size of the joined region under the unit range. Since the size of the joined region and the strength of the joined object have a one-to-one relationship with each other, the joining strength of the joined object can be estimated in accordance with the integrated feature's value of the observed reflected wave in the unit range and the preset relation of conversion. In such a manner, by estimating the joining strength of the joined object based on the integrated feature of the observed reflected wave in the unit range, the joining strength of the joined object can be readily estimated without a need for obtaining the size of the joined region.

Additionally, the present invention may feature that, in the reflected wave measuring step, the ultrasonic wave is introduced into the joined object at a plurality of different angles of refraction.

According to this invention, even in the case in which a hooking phenomenon occurs upon the friction stir joining process, a reflected echo from a hooking portion can be caught by an angle beam method. Therefore, the precision of estimation for the joined region and/or joining strength can be enhanced.

The present invention is a method of estimating a joining strength of a joined object in which two joining members are joined together while being overlapped one on another by using a friction stir joining method, comprising:

a reflected wave measuring step of introducing an ultrasonic beam having a cross section greater than a joined region diameter, by using a vertical oscillator, into the joined object from a face of the joined object opposed to an plunging face thereof in which a joining tool was plunged upon a friction stir process, and taking in a reflected wave of the ultrasonic wave introduced into and reflected from the joined object; and a strength estimation step of estimating the joining strength of the joined object, based on a reflected echo level obtained by the reflected wave measuring step.

According to this invention, the joining strength of the joined object can be estimated with a simple and low-cost method.

The present invention is a method of testing a joined object in which two joining members are joined together while being overlapped one on another by using a friction stir joining method, the testing method comprising the step of inspecting the joined object based on an estimation result obtained by the estimation method described above.

According to this invention, the joined object is inspected based on the estimation by the estimation method described above. Consequently, the inspection for the joined region and/or joining strength can be performed without destroying the joined object, as such facilitating the inspection work.

The present invention is an apparatus for estimating a joined region of a joined object in which two joining members are joined together while being overlapped one on another by using a friction stir joining method, comprising:

an ultrasonic probe configured to introduce an ultrasonic wave into the joined object and also take in a reflected wave reflected from the joined object;

probe moving means configured to scan the ultrasonic probe over a face of the joined object opposed to an plunging face thereof in which a joining tool was plunged, such that the ultrasonic probe passes through over the joined region of the joined object;

scanning position detection means configured to detect a scanning position of the probe;

extraction means connected with the ultrasonic probe and configured to extract an observed reflected wave reflected in a vicinity of a position corresponding to an interface between the two joining members, among reflected waves taken in by the ultrasonic probe;

storage means configured to correlate the scanning position detected by the scanning position detection means with the observed reflected wave extracted by the extraction means corresponding to the scanning position and store them therein;

estimation means configured to read information stored in the storage means and estimate the scanning position corresponding to the observed reflected wave satisfying a predetermined boundary condition, as a position over the joined region; and output means configured to output an estimation result obtained by the estimation means.

According to this invention, the ultrasonic wave is introduced into the joined object from the face opposed to the plunging face in which the joining tool was plunged, while the ultrasonic wave reflected from the joined object is taken in, by the ultrasonic probe. In this state, the probe moving means scans the ultrasonic probe such that it passes through over the joined region of the joined object. The extraction means extracts the observed reflected wave, for each scanning position, during a period of time the ultrasonic probe is moved by the probe moving means. The storage means correlates the scanning position detected by the scanning position detection means with the observed reflected wave extracted by the extraction means corresponding to the scanning position and then stores them therein.

A feature or features of the observed reflected wave will change between the case in which the ultrasonic wave incident position is located over the non-joined region and the case in which the same incident position is located over the joined region. The estimation means estimates the scanning position in which the observed reflected wave satisfies the predetermined boundary condition as a position in which the ultrasonic wave incident position is over the joined region. The output means outputs the estimation result obtained by the estimation means.

In this invention, the ultrasonic wave is introduced into the joined object from the face opposed to the plunging face in which the joining tool was plunged, while the joined region is estimated by observing the reflected wave of the ultrasonic wave in the vicinity of the position corresponding to the interface between the two joining members. Consequently, the joined region can be estimated, without being affected by the concave/convex shape of the joining tool plunging face. This can also prevent the ultrasonic probe from contacting with the tool plunging mark of the joined object, thereby avoiding damage of the ultrasonic probe. Due to the output of the estimation result for the joined region, the quality of joining can be known without destroying the joined object, as such reducing the cost required for the quality inspection as compared with the case requiring the destructive inspection.

The present invention is an apparatus for inspecting a joined object in which two joining members are joined together while being overlapped one on another by using a friction stir joining method, comprising:

an ultrasonic probe configured to introduce an ultrasonic wave into the joined object and also take in a reflected wave reflected from the joined object;

probe moving means configured to scan the ultrasonic probe over a face of the joined object opposed to an plunging face thereof in which a joining tool was plunged, such that the ultrasonic probe passes through over the joined region;

scanning position detection means configured to detect a scanning position of the probe;

extraction means connected with the ultrasonic probe and configured to extract an observed reflected wave reflected in a vicinity of a position corresponding to an interface between the two joining members, among reflected waves taken in by the ultrasonic probe;

storage means configured to correlate the scanning position detected by the scanning position detection means with the observed reflected wave extracted by the extraction means corresponding to the scanning position;

estimation means configured to read information stored in the storage means and estimate the scanning position corresponding to the observed reflected wave satisfying a predetermined boundary condition as a position over the joined region;

judging means configured to judge whether or not the joined object satisfies a predetermined quality, based on an estimation result obtained by the estimation means; and output means configured to output a judging result obtained by the estimation means.

According to this invention, by the ultrasonic probe, the ultrasonic wave is introduced into the joined object from the face opposed to the plunging face in which the joining tool was plunged, while the ultrasonic wave reflected from the joined object is taken in. In this state, the probe moving means scans the ultrasonic probe such that it passes through over the joined region of the joined object. The extraction means extracts the observed reflected wave, for each scanning position, during a period of time the ultrasonic probe is moved by the probe moving means. The storage means correlates the scanning position detected by the scanning position detection means with the observed reflected wave extracted by the extraction means corresponding to the scanning position and then stores them therein.

A feature or features of the observed reflected wave will change between the case in which the ultrasonic wave incident position is located over the non-joined region and the case in which the same incident position is located over the joined region. The estimation means estimates the scanning position in which the observed reflected wave satisfies the predetermined boundary condition as a position in which the ultrasonic wave incident position is over the joined region. The judging means judges whether or not the joined object satisfies the predetermined quality, based on the estimation result obtained by the estimation means. The output means outputs the estimation result obtained by the estimation means.

In this invention, the joined region is estimated by introducing the ultrasonic wave into the joined object from the face opposed to the plunging face in which the joining tool was plunged, while observing the reflected wave of the ultrasonic wave in the vicinity of the position corresponding to the interface between the two joining members. Consequently, the quality of the joined object can be inspected, without being affected by the concave/convex shape of the joining tool plunging face and without destroying the joined object.

BEST MODE FOR CARRYING OUT THE INVENTION

Figure 1:
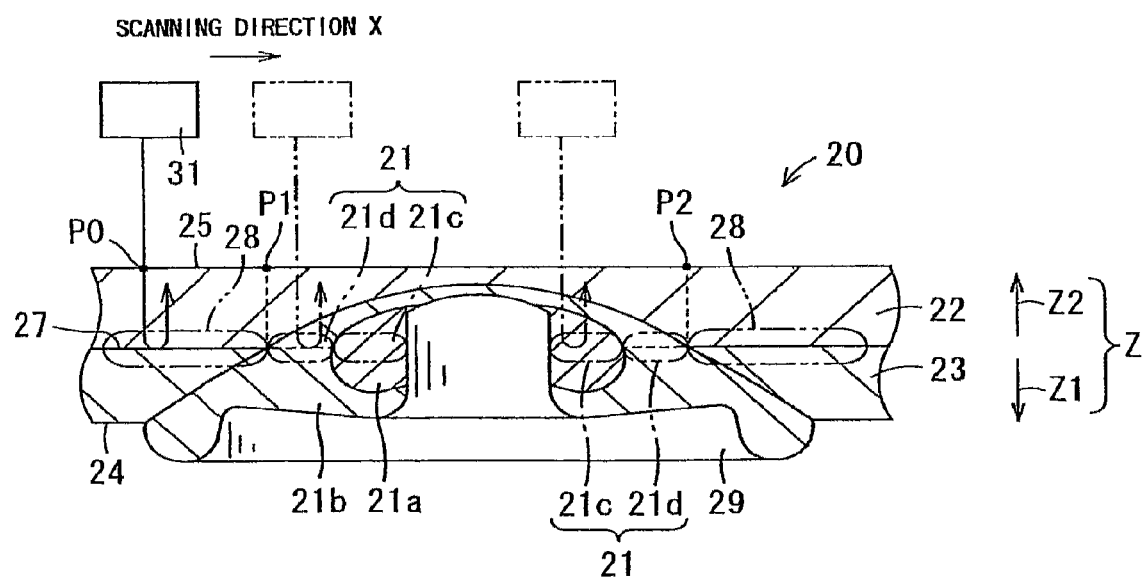
FIG. 1 is a section for illustrating an estimation method for a joined region 21 of a joined object 20, this method being a first embodiment of the present invention.

An estimation method for a joined region of a joined object, according to a first embodiment of the present invention, is used for estimating the joined region 21 of the joined object 20 shown in FIG. 1. In this embodiment, the joined object 20 is formed by joining two members 22, 23 together along the reference directions Z, by utilizing the friction stir joining method, these two members 22, 23 having been put one on another in advance along the reference directions Z.

In the spot friction stir joining method, a joining tool is pressed into a tool plunging face 24 that is a surface located in one reference direction Z1 of the joining member 23 located in the one reference direction Z1 of the two joining members 22, 23 while the joining tool is rotated. Consequently, frictional heat is generated between the joining tool and the one joining member 23 so as to soften the one joining member 23. Thus, a distal end of the joining tool is pressed into and plunged through the one joining member 23 until it reaches the other joining member 22. At this time, softened portions of the respective joining members 22, 23 are plastically flowed about a rotation axis with the joining tool. After the respective softened portions of the joining members 22, 23 are plastically flowed, the joining tool is withdrawn from the joining members 22, 23 in the one reference direction Z1.

The joining tool is designed to include a generally cylindrical pin portion and a generally cylindrical shoulder portion connected with one end of the pin portion and formed coaxially with the pin portion. The diameter of the shoulder portion is formed to be larger as compared with the diameter of the pin portion. The joining tool is configured to be plunged into the tool plunging face 24 of the one joining member 23 from its pin portion as a distal portion. In a state in which the pin portion extends through the one joining member 23 and is plunged in the other joining member 22, the shoulder portion is also plunged in the one joining member 23 and is pressed against the other joining member 23.

Due to such plastic flowing of interfacial portions of the respective joining members 22, 23, the two joining members 22, 23 will be mixed together by friction stirring in the vicinity of an interface thereof. As a result, the interface 27 between the two joining members 22, 23 will disappear, and hence the two joining members 22, 23 are metallurgically integrated. Thus, a portion, in which the interface between the two joining members 22, 23 has disappeared, will be referred to as the joined region 21 of the two joining members 22, 23.

The joined object 20 after the joining process is formed to include a stirred portion 21a and a heat-influenced portion 21b. The stirred portion 21a corresponds to a portion which was rotated with the pin portion and plastically flowed upon the friction stirring. Namely, the stirred portion 21a corresponds to the portion which was adjacent to or facing the pin portion of the joining tool upon the friction stirring, and is formed into a substantially ring-like shape, coaxially with the axis of a joining mark 29. In addition, the stirred portion 21a has a structure in which metal crystal grains of a metallographic structure are formed more finely as compared with the remaining portion. The heat-influenced portion 21b corresponds to a portion which was formed into a substantially ring-like shape covering the stirred portion 21a. Namely, the heat influenced portion 21b corresponds to the portion which was softened upon the friction stirring due to heat applied from the stirred portion 21a and the joining tool.

In the joined object 20, the joined region 21, which contributes to the joining strength, is formed. The joining region 21 is configured to include a stir-joined region 21c and a pressure-joined region 21d. The stir-joined region 21c corresponds to a part of the stirred portion 21a, which has disappeared as a melted mixture of the interfacial portions between the upper plate 22 and the lower plate 23, the melted mixture being mainly caused by stirring due to plastic flowing. The pressure-joined region 21d corresponds to a part of the heat-influenced portion 21b. The pressure-joined region 21d has been formed in the portion where the interfacial portions between the upper plate 22 and the lower plate 23 disappeared mainly due to the influence of the softening of each plate 22, 23 by the frictional heat and the pressing by the shoulder portion of the joining tool. The stir-joined region 21c and the pressure-joined region 21d are formed in a position, in which the interface between the respective plates 22, 23 has existed before the joining process, and have a ring-like shape coaxial with the axis of the joining mark 29, respectively. The size of such a joined region 21 will have a substantial effect on the joining strength of the joined object 20.

In the joined object 20 after the joining process, the joining mark 29 of the joining tool remains as the concave/convex shape formed in the surface on the side of the one reference direction Z1 of the joining member 23 located in the one reference direction Z1. The joining mark 29 is a generally concave cylindrical portion which opens in one direction and has a bottom portion. In the joined object 20, a backing face 25 opposed to the tool plunging face 24 is maintained as a flat face. Hereinafter, the joining member 22 located in the other reference direction Z2 will also be referred to as the upper plate 22, and the joining member 23 located in the one reference direction Z1 will also be referred to as the lower plate 23. In addition, a region other than the joined region 21 will be referred to as a non-joined region 28. In the non-joined region 28, the upper plate 22 and the lower plate 23 are not joined together, and the interface 27 exists between the upper plate 22 and the lower plate 23.

As shown in FIG. 1, in this embodiment, by using the ultrasonic probe 31, an ultrasonic wave is radiated or introduced into the joined object 20 from the backing face 25 of the joined object 20 opposed to the tool plunging face 24 thereof in which the joining tool was plunged upon the friction stir process, while a reflected wave of the ultrasonic wave introduced in the joined object 20 is taken in. The ultrasonic wave generated by the ultrasonic probe 31 is scanned such that each position in which the ultrasonic wave is introduced is located along a predetermined scanning direction X and such that the ultrasonic wave passes through over the joined region 21 of the joined object 20.

In the estimation method of this embodiment, the joined region 21 is estimated based on changing amounts of amplitude of an observed reflected wave reflected in the vicinity of a position corresponding to the interface 27 of the two joining members 22, 23, among the reflected waves taken in due to the ultrasonic probe 31. Hereinafter, the amplitude of the observed reflected wave will be referred to as an echo level. Namely, the echo level is the maximum amplitude of the observed reflected wave and corresponds to the intensity of the observed reflected wave. In this embodiment, a scanning position measured when the echo level becomes lower than a predetermined threshold value is estimated as a position over the joined region 21.

Figure 2:
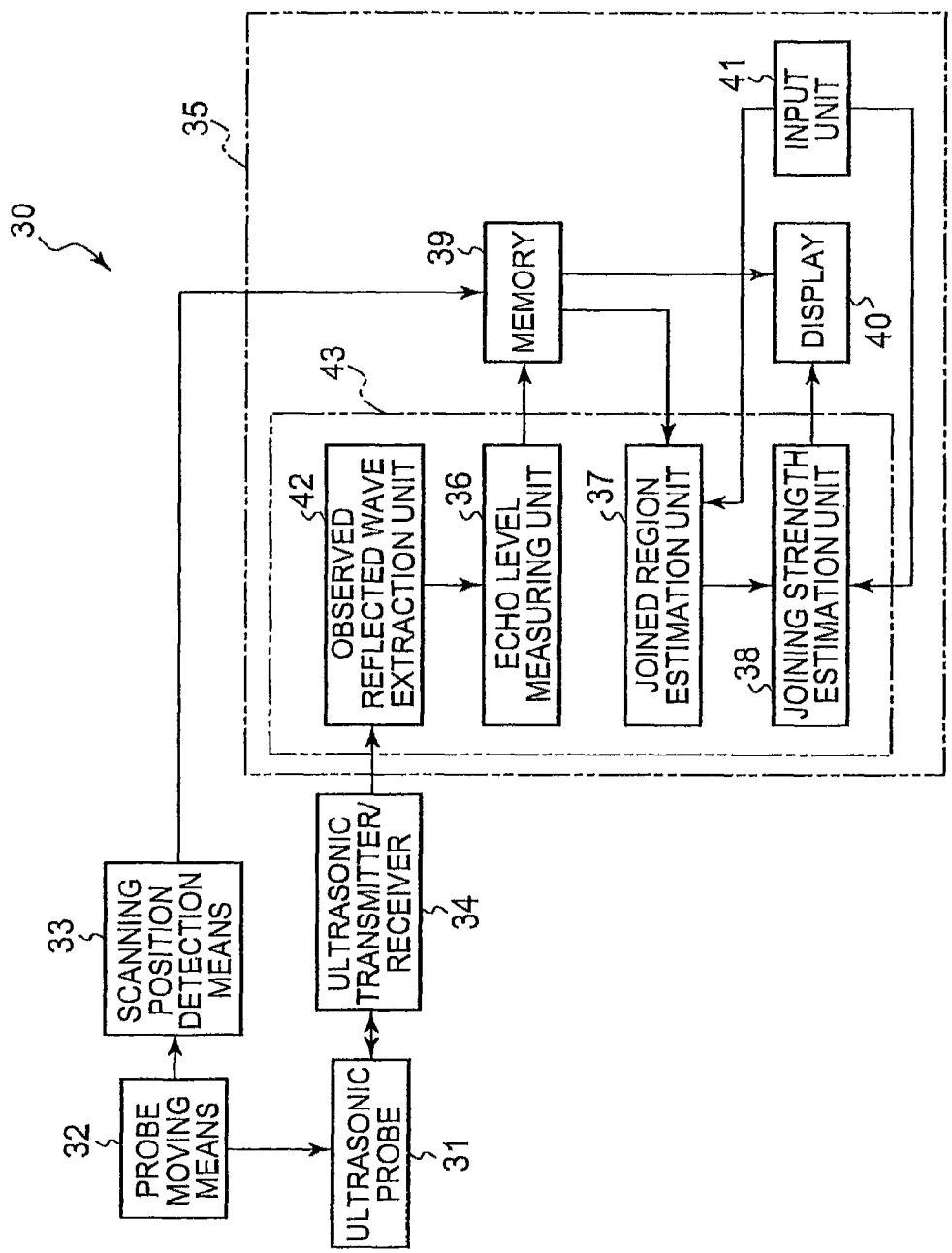
FIG. 2 is a block diagram showing an estimation apparatus 30 for the joined region 21.

FIG. 2 is a block diagram showing the estimation apparatus 30 for estimating the joined region 21. In this embodiment, the estimation apparatus 30 is also configured to estimate the joining strength, which is also referred to as joint strength, of the joined object 20. In this embodiment, the joining strength of the joined object 20 is regarded as strength measured when pulling force is applied to rip off the upper plate 22 from the lower plate 23 in the reference directions Z or as strength measured when shearing force is applied to the upper plate 22 and lower plate 23 in a direction vertical to the reference directions Z.

The estimation apparatus 30 is configured to include the ultrasonic probe 31, a probe moving means 32, a scanning position detection means 33, an ultrasonic transmitter/receiver 34, and a computer 35. The ultrasonic probe 31 is configured to include an electric sound converter element, which is adapted to generate an ultrasonic wave when vibrated due to application thereto of a pulsed electric signal from the ultrasonic transmitter and receiver 34. In addition, the ultrasonic probe 31 is configured to be vibrated when receiving an ultrasonic wave, so as to generate a pulsed electric signal corresponding to the vibration, thus providing the generated electric signal to the ultrasonic transmitter and receiver 34. The ultrasonic probe 31 is also configured such that it can introduce the ultrasonic wave into the joined object 20 as well as it can take therein the reflected wave reflected from the interior of the joined object 20.

In this embodiment, the ultrasonic probe 31 is a single probe which can transmit and receive the ultrasonic wave, having a beam diameter of 0.8×0.5 mm and is adapted to generate the ultrasonic wave having a frequency of 17 MHz. Between the ultrasonic probe 31 and the joined object 20, a contact medium is placed for transmitting and receiving the ultrasonic wave. For instance, the contact medium is a water bag filled with water, a liquid like water, or a jerry-like material such as glycerin or the like.

The probe moving means 32 is configured to displace the ultrasonic probe 31. In this embodiment, the probe moving means 32 scans the ultrasonic probe 31 over the backing face 25 of the joined object 20, such that the ultrasonic probe 31 can pass through over the joined region 21 of the joined object 20. Specifically, the probe moving means 32 is configured to drive and displace the ultrasonic probe 31 in a first direction vertical to the reference directions Z as well as in a second direction vertical to both of the reference directions Z and the first direction. More specifically, the probe moving means 32 scans the ultrasonic probe 31, while keeping an incident direction of the ultrasonic wave vertical to the backing face 25. The scanning position detection means 33 is configured to detect a scanning position of the ultrasonic probe 31. The scanning position detection means 33 provides a scanning position signal indicative of the scanning position of the ultrasonic probe 31 to the computer 35.

The ultrasonic transmitter and receiver 34 provides the pulsed electric signal to the ultrasonic probe 31 so as to vibrate the ultrasonic probe 31. Besides, the ultrasonic transmitter and receiver 34 is configured to amplify the pulsed electric signal provided from the ultrasonic probe 31 and corresponding to the reflected wave, convert the electric signal into a reflected wave signal indicative of the reflected wave taken in the ultrasonic probe 31, and provide the reflected wave signal to the computer 35. The reflected wave signal is indicative of changes over time of the amplitude of the ultrasonic wave taken in the ultrasonic probe 31.

The computer 35 is configured to include an observed reflected wave extraction unit 42, an echo level measuring unit 36, a joined region estimation unit 37, a joining strength estimation unit 38, a memory or storage means 39, an input unit 41, and a display 40. The observed reflected wave extraction unit 42 is configured to extract the observed reflected wave reflected in the vicinity of a position corresponding to the interface between the two joining members, based on the reflected wave signal provided from the ultrasonic transmitter and receiver 34, for each displacement of the scanning position of the ultrasonic probe 31. The echo level measuring unit 36 is configured to measure the echo level that is the amplitude of the observed reflected wave, based on the result of extraction due to the observed reflected wave extraction unit 42, for each displacement of the scanning position of the ultrasonic probe 31, and send the measured echo level to the memory 39 in order to store it therein.

The memory 39 receives a scanning position signal from the scanning position detection means 33. The memory 39 is configured to store therein the scanning position of the ultrasonic probe 31 detected by the scanning position detection means 33, in relation to the echo level measured by the echo level measuring unit 36, corresponding to the scanning position. The joined region estimation unit 37 is configured to read information stored in the memory 39 and estimate the scanning position that satisfies a predetermined boundary condition, as a position located over the joined region 21. The joining strength estimation unit 38 is configured to estimate the size of the joined region 21, based on the position over the joined region 21 estimated by the joined region estimation unit 37, and further estimate the joining strength, based on a one-to-one relationship with the estimated size.

The display 40 is configured to display information indicative of the echo level stored in the memory 39 and the scanning position stored therein in relation to the echo level. The display 40 also displays the joining strength estimated by the joining strength estimation unit 38. The input unit 41 is configured such that the predetermined boundary condition required for estimation of the joined region 21 is introduced thereto as well as configured to provide the introduced boundary condition to the joined region estimation unit 37. Additionally, the input unit 41 is configured such that the information indicative of the relationship, between the size of the joined region 21 and the joining strength, necessary for estimation of the joining strength, is introduced thereto as well as configured to provide the introduced relational information to the joining strength estimation unit 38. In this embodiment, the echo level extraction unit 36, joined region estimation unit 37 and joining strength estimation unit 38 can be achieved by performing operating programs stored in a preset memory circuit by using a processor circuit 43, such as a central processing unit (CPU).

Figure 3:
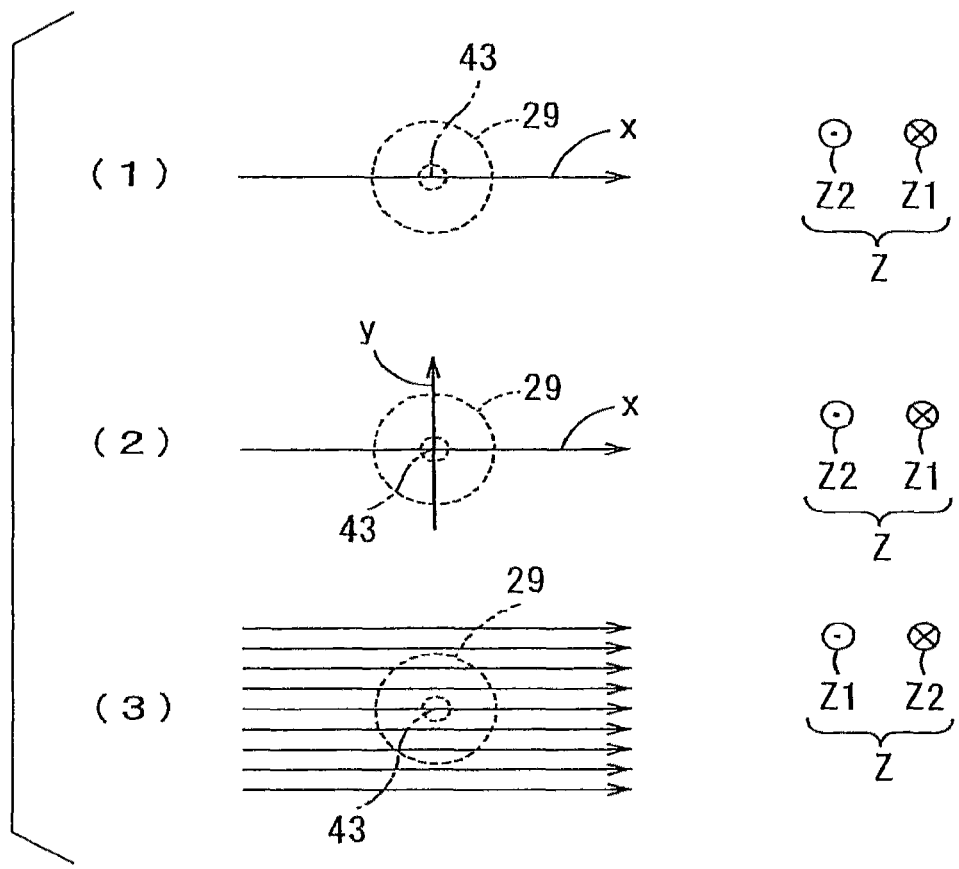
FIG. 3 is a diagram showing a transfer route of an ultrasonic probe 31 moved by a probe moving means 32.

FIG. 3 is a diagram showing a transfer route of the ultrasonic probe 31 moved by the probe moving means 32. As shown in FIG. 3(1), the probe moving means 32 causes the ultrasonic probe 31 to move in the scanning direction vertical to the reference directions Z such that it can pass through over a central position 43 of the joining mark 29. Specifically, the probe moving means 32 moves the ultrasonic probe 31 in one scanning direction, from a position sufficiently far away from the joined region 21 on one side along the scanning direction to a position sufficiently far away from the joined region 21 on the other side along the scanning direction. In other words, the probe moving means 32 moves the ultrasonic probe 31 from a position over one non-joined region 28 adjacent to the joined region 21 on one side along one scanning direction, such that the ultrasonic probe 31 passes through over the joined region 21 in the scanning direction and then reaches the other non-joined region 28 adjacent to the joined region 21 on the other side along the scanning direction. It is noted that each non-joined region 28 is a region including the interface 27 present between the two joining members 22, 23.

Alternatively, as shown in FIG. 3(2), the ultrasonic probe 31 may be moved both in a first scanning direction X and in a second scanning direction Y. The first and second directions X, Y are respectively defined to pass through over the central position 43 of the joining mark 29 and extend vertically to the reference directions Z and orthogonally to each other. Also in this case, the ultrasonic probe 31 is scanned to pass through over the joined region 21 along the backing face 25 in both of the first and second directions.

Alternatively, as shown in FIG. 3(3), the ultrasonic probe 31 may be moved along the backing face 25 so as to be scanned over the whole two-dimensional surface area set in advance to include a region spreading over the joined region 21. For instance, the ultrasonic probe 31 may be first moved in a main scanning direction vertical to the reference directions Z, then shifted in a sub-scanning direction vertical to the main scanning direction, and thereafter moved again in the main scanning direction. Furthermore, by repeating such operations, the ultrasonic probe 31 may be scanned over the preset whole two-dimensional surface area.

Figure 4:
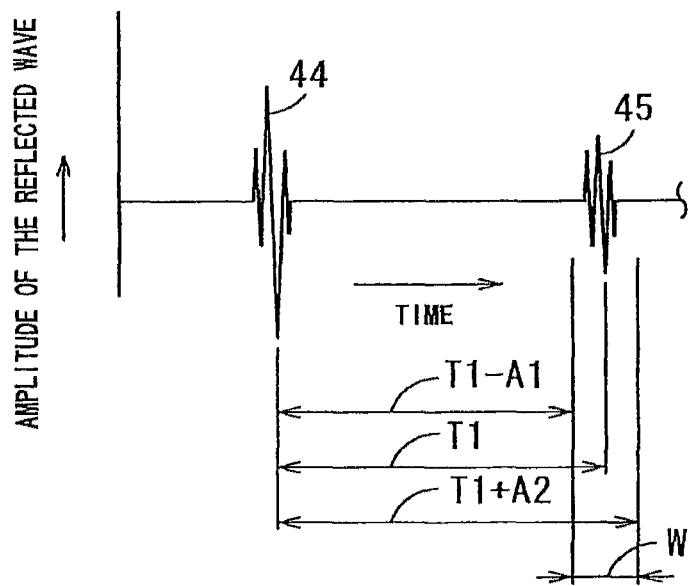
FIG. 4 is a diagram showing a wave form of an ultrasonic reflected wave reflected from the joined object 20.

FIG. 4 is a diagram showing a wave form of an ultrasonic reflected wave reflected from the joined object 20. In FIG. 4, time is expressed on the horizontal axis, while the amplitude is designated on the vertical axis. When the scanning position is located over the non-joined region 28, the reflected wave will include a reflected wave 44 reflected at the backing face 25 that is a top face of the upper plate 22 and the reflected wave 45 reflected at the interface 27 between the upper plate 22 and the lower plate 23.

The observed reflected wave extraction unit 42 obtains a reference time T1 defined between the time the reflected wave 44 reflected from the top face 25 of the upper plate 22 reaches the ultrasonic probe 31 and the time the reflected wave 45 reflected from the interface 27 between the upper plate 22 and the lower plate 23 reaches the ultrasonic probe 31, base on the reflected wave signal provided from the ultrasonic transmitter/receiver 34. In addition, the observed reflected wave extraction unit 42 sets a gate interval W defined across the reference time T1. Specifically, the gate interval W is set as a time interval defined from the time (T1−A1) set earlier than the reference time T1 to the time (T1+A2) set later than the reference time T1. The observed reflected wave extraction unit 42 is configured to extract each reflected wave taken in the ultrasonic probe 31 during the gate interval W, as the observed reflected wave 45 reflected in the vicinity of a position, in the reference directions Z, corresponding to the interface 27 between the two joining members 22, 23. Then, the echo level measuring unit 36 outputs the amplitude that is the highest of the observed reflected waves extracted over the gate interval W, as the echo level.

Figure 5:
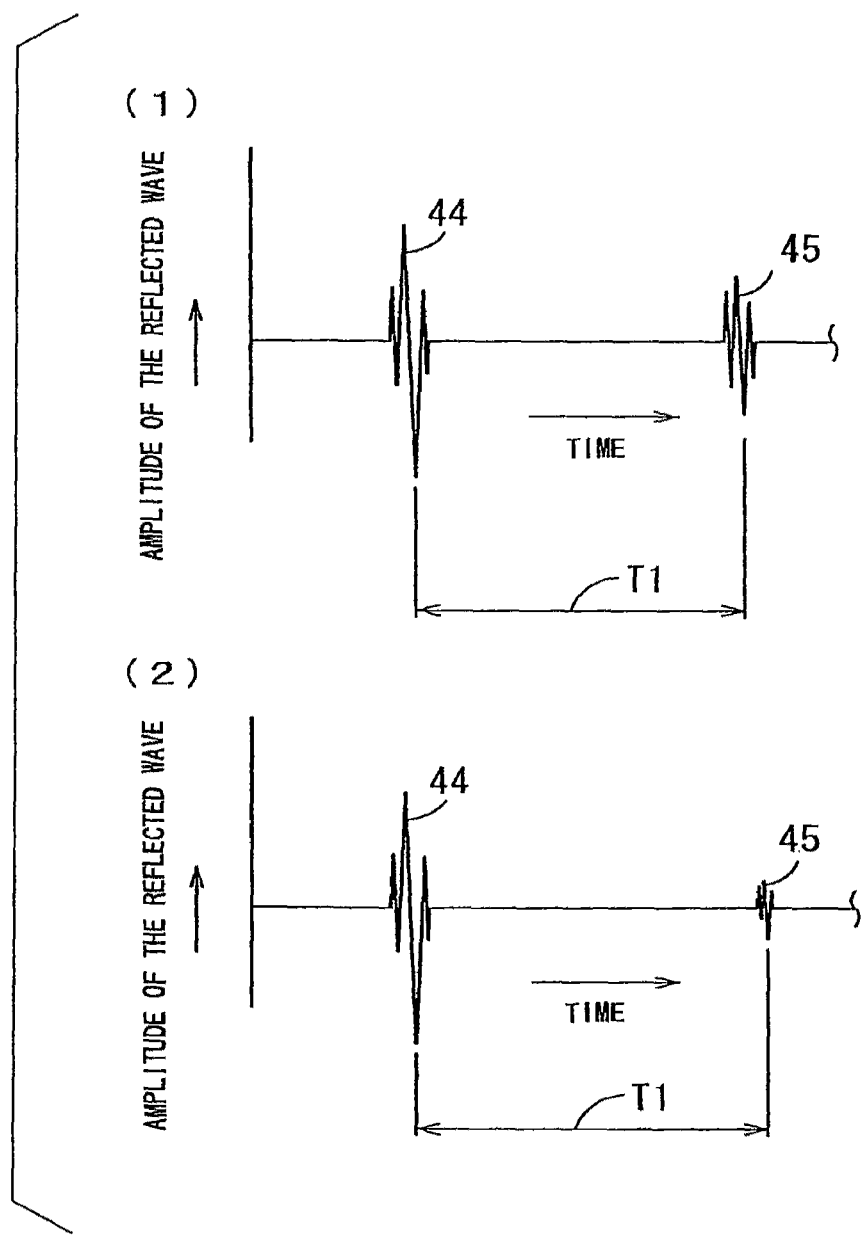
FIG. 5 is a diagram for illustrating changes of the wave form of the reflected wave, relative to changes of a scanning position.

FIG. 5 is a diagram for illustrating changes of the wave form of the reflected wave, relative to changes of the scanning position. FIG. 5(1) illustrates the wave form of the reflected wave when the scanning position is over the non-joined region 28. FIG. 5(2) illustrates the wave form of the reflected wave when the scanning position is over the joined region 21.

In the non-joined region 28, since the interface 27 exists between the upper plate 22 and the lower plate 23, the ultrasonic wave introduced from the upper plate 22 is reflected from the interface 27 between the upper plate 22 and the lower plate 23. Contrary, in the joined region 21, since the interface 27 between the upper plate 22 and the lower plate 23 has disappeared, the reflected wave introduced from the upper plate 22 is transmitted through the lower plate 23 without being reflected in the upper plate 22.

Accordingly, as shown in FIG. 5(1), when the scanning position is located over the non-joined region 28, the reflected wave reflected from the interface 27 between the upper plate 22 and the lower plate 23 is relatively great, rendering the echo level of the observed reflected wave 45 significantly higher. Contrary, as shown in FIG. 5(2), when the scanning position is over the joined region 21, the reflected wave reflected from a position in the reference directions corresponding to the interface 27 between the upper plate 22 and the lower plate 27 is substantially reduced, thus lowering the echo level of the observed reflected wave 45.

Figure 6:
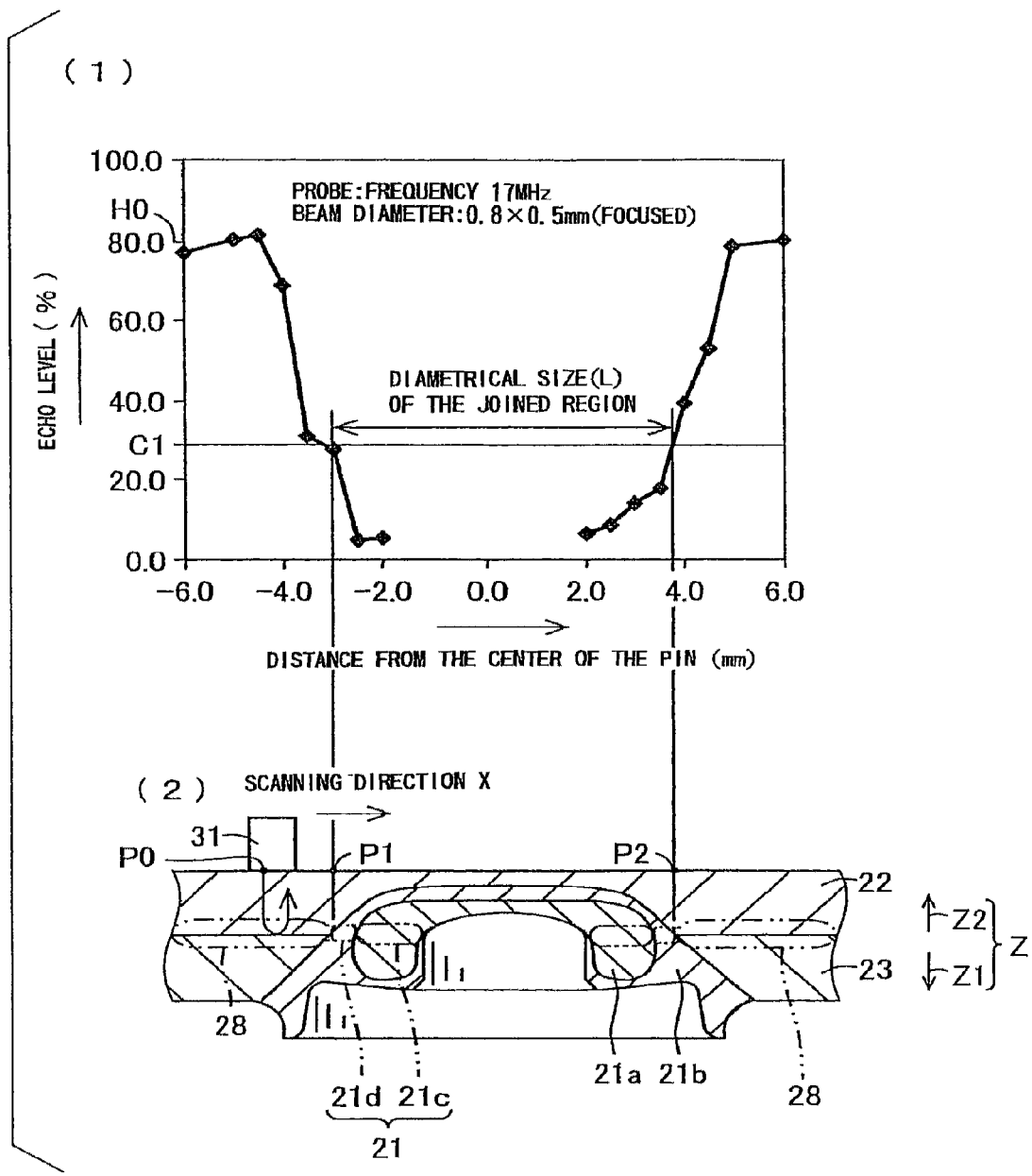
FIG. 6 is a diagram for illustrating changes of an echo level, relative to the changes of the scanning position.

FIG. 6 is a diagram for illustrating changes of the echo level, relative to the changes of the scanning position. FIG. 6(1) illustrates the changes of the echo level, relative to the changes of the scanning position, and FIG. 6(2) is a section of the joined object 20 corresponding to the graph of FIG. 6(1). In FIG. 6(1), the scanning position is expressed on the horizontal axis, while the echo level is designated on the vertical axis. More specifically, in FIG. 6(1), a percentage of the echo level for each scanning position relative to a reference echo level H0 is expressed on the vertical axis. The reference echo level H0 corresponds to the echo level when the scanning position is located over the non-joined region 28.

As shown in FIG. 3(1), when the ultrasonic probe 31 is scanned in the scanning direction such that it can pass through the center of the joining mark 29, the scanning position, in which the echo level measured for each scanning position is lower than a preset level threshold value C1, can be estimated as a position over the joined region 21, as shown in FIG. 6(1).

In addition, a scanning position P1 in which the echo level for each scanning position is switched from a state higher than the level threshold value C1 to a state lower than the same threshold value and a scanning position P2 in which the echo level is switched from the state lower than the level threshold value C1 to the state higher than the same threshold value can be estimated as positions over the boundary between the joined region 21 and the non-joined region 28, respectively. Furthermore, the length of a line connecting the two scanning positions P1, P2 over the respective boundary positions can be estimated as a diametric size of the joined region 21.

The level threshold value C1 that is the boundary condition for judging whether or not the scanning position is located over the joined region 21 is determined, based on the observed reflected wave when the ultrasonic wave incident position is located over the non-joined region 28. Namely, the level threshold value C1 is set lower than the echo level measured when the ultrasonic wave incident position is located over the non-joined region 28. For instance, the level threshold value C1 is determined based on a function of variables including a plate thickness t1 of the upper plate 22, a plate thickness t2 of the lower plate 23, a factor L1 related to joining conditions, a factor L2 related to the tool shape, and a factor L3 related to materials (i.e., C1=f(t1, t2, L1, L2, L3). In other words, the level threshold value C1 is set lower than the reference echo level H0 and defined as the echo level measured when the scanning position is located over the boundary between the joined region 21 and the non-joined region 28. In this embodiment, the level threshold value C1 is determined based on a function of variables including the plate thickness t1 of the upper plate 22 and the reference echo level H0. In this case, the level threshold value C1 is set at a level obtained by lowering the reference echo level H0 by $-\alpha-20 \log(t2^{1/2})$ decibels. As described above, the factor t2 is the plate thickness of the lower plate 23. Again, the reference echo level H0 is set as an echo level when the scanning position is located over the non-joined region 28. The variable $\alpha$ is a constant, and in this embodiment, $\alpha=9$.

Alternatively, when the reference echo level is expressed as H0, the level threshold value C1 may be set as H0×β. In this case, β is a constant, and in this embodiment, it is set at, for example, 0.35. It is noted that the variables $\alpha$, $\beta$ may be optionally altered depending on the joining materials, joining conditions, shape of the joining tool and the like and may be experimentally determined in advance prior to the estimation.

Figure 7:
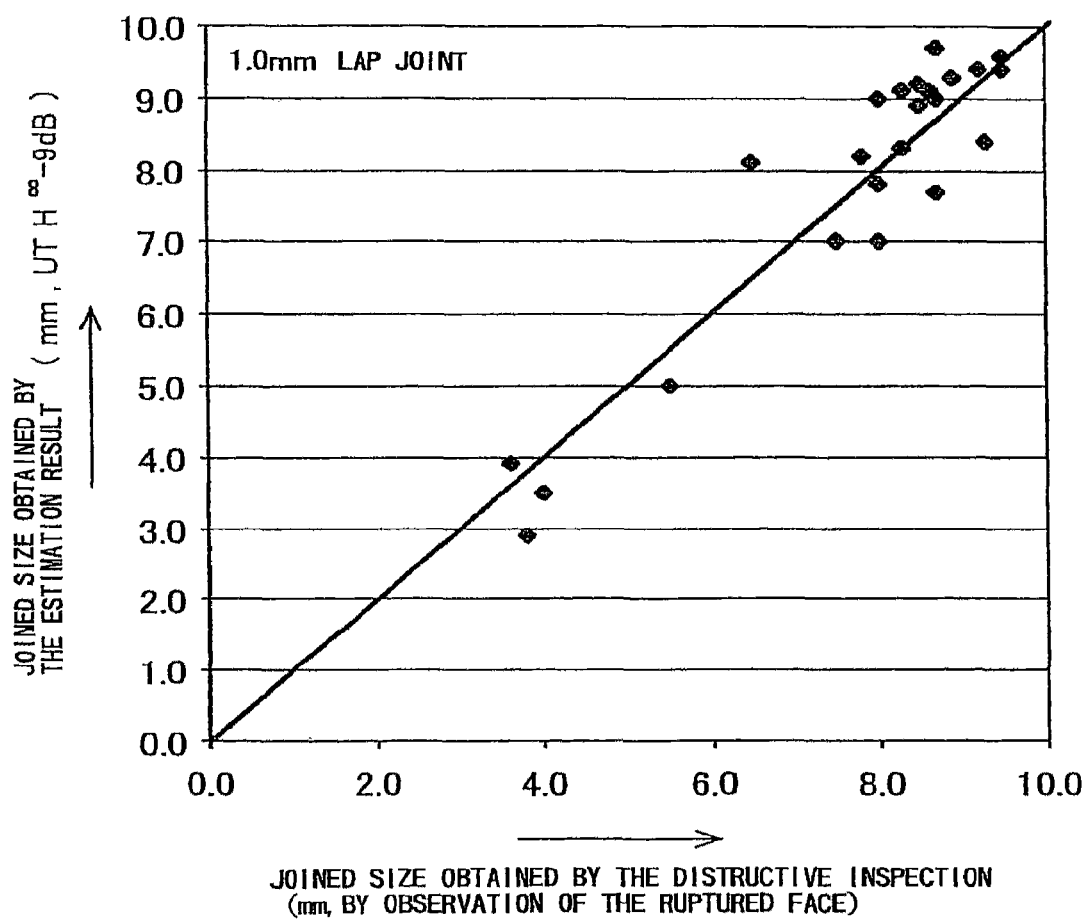
FIG. 7 is a graph for showing a comparison of distribution of a diametric size of the estimated joined region 21 with the diametric size of the joined region 21 obtained by observation of a ruptured face thereof after estimation.
Figure 8:
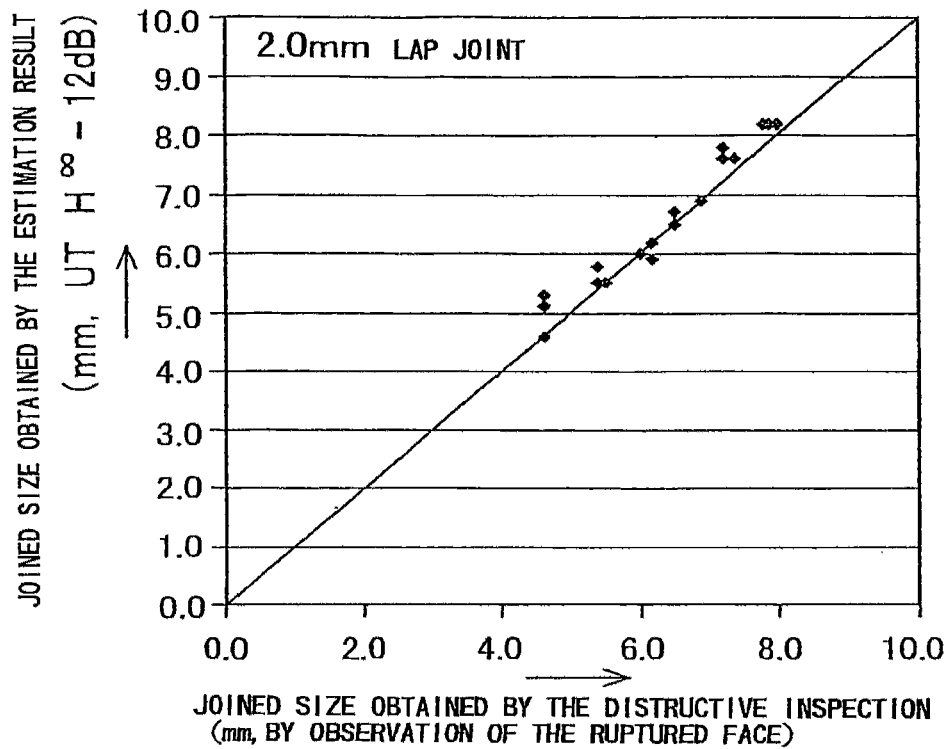
FIG. 8 is a graph for showing a comparison of the distribution of the diametric size of the estimated joined region 21 with the diametric size of the joined region 21 obtained by observation of the ruptured face thereof after the estimation.

FIG. 7 and FIG. 8 are graphs for respectively showing a comparison of distribution of a diametric size of the estimated joined region 21 (solid line) with the diametric size of the joined region 21 obtained by observation of a ruptured face thereof after estimation. In each of FIGS. 7 and 8, the diametric size of the joined region 21 obtained by observation of the ruptured face is expressed on the horizontal axis, while the estimated joined region 21 is designated on the vertical axis. FIG. 7 shows a case in which the plate thickness of each plate 22, 23 is 1 mm, while FIG. 8 shows a case in which the plate thickness of each plate 22, 23 is 2 mm. As shown in FIGS. 7 and 8, it is found that the observation result obtained from the ruptured face has correlatively with the estimation result.

Accordingly, with the estimation method as described above, the diametric size L of the joined region 21 can be estimated without destroying the joined object 20.

Figure 9:
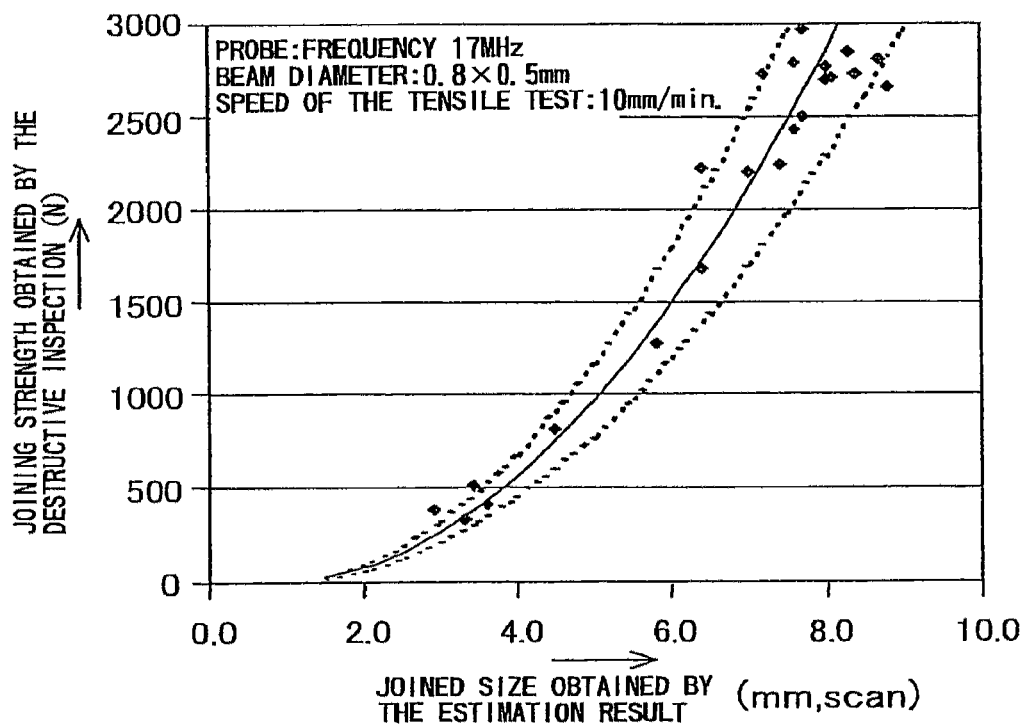
FIG. 9 is a graph for showing distribution of the joining strength of the joined object measured by a destructive inspection, relative to the diametric size of the estimated joined region 21.

FIG. 9 is a graph for showing distribution of the joining strength of the joined object measured by a destructive inspection, relative to the diametric size of the estimated joined region 21. In this case, the joining strength that is estimated based on each average value of the diametric size of the estimated joined region is shown by a solid line, while the joining strength that is estimated based on each value obtained by changing ±20% the average value of the estimated diametric size of the joined region is shown by broken lines, respectively. As shown in FIG. 9, there is a one-to-one mutual relation between the estimated diametric size L of the joined region 21 and the joining strength. Accordingly, with preparation of a computing equation or data base expressing the relationship between the previously estimated diametric size L of the joined region 21 and the joining strength, the joining strength can be calculated, in accordance with such a computing equation or data base, from the estimated joined region 21. For instance, when the estimated diametric size of the joined region 21 is expressed as L, the joining strength will be generally expressed by $K1 \cdot L^2$. In this case, K1 is a predetermined constant, which can be experimentally obtained.

Figure 10:
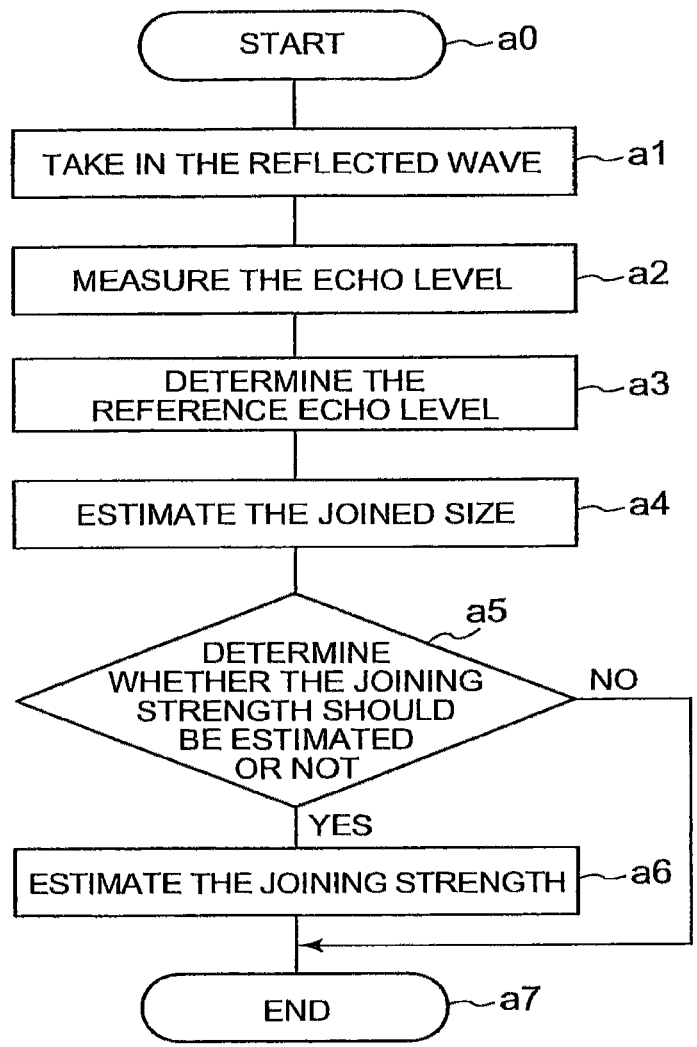
FIG. 10 is a flow chart showing a procedure of the estimation method for estimating the joining strength.

FIG. 10 is a flow chart showing a procedure of the estimation method of estimating the joining strength. First, in a step a0, the joined object having been subjected to the spot friction stir joining process is prepared and the estimation apparatus 30 is also prepared. In addition, a relational expression for obtaining the level threshold value C1 is experimentally obtained from the reference echo level, while the relational expression for estimating the joining strength is experimentally obtained from the diametric size L of the estimated joined region 21. Besides, whether or not the joining strength should be estimated is determined. Once such preparations required for the estimation work for the joined object has been completed, the procedure goes to a step a1, in which the estimation work is started.

In the step a1, a reflected wave measuring step is performed, in which the reflected wave generated when the ultrasonic wave is introduced into the joined object 20 by the ultrasonic probe 31 is measured. Then, the reflected wave is taken in the ultrasonic probe 31 while the ultrasonic probe 31 is scanned by the probe moving means 32. In this way, once the reflected wave has been measured for each scanning position with the ultrasonic probe 31 being scanned, the procedure goes to a step a2.

In the step a2, the observed reflected wave is extracted for each predetermined microscopic scanning position, from the reflected waves, by using the observed reflected wave extraction unit 42. Subsequently, by using the echo level measuring unit 36, the echo level of the observed reflected wave extracted for each scanning position is measured. Optionally, the observed reflected wave extraction unit 42 may determine the gate interval W for capturing the observed reflected wave, based on the plate thickness of the upper plate 22 introduced from the input unit 41. In this manner, once the step of measuring the echo level for each scanning position has been completed, the procedure goes to a step a3.

In the step a3, the reference echo level H0 when the scanning position is located over the non-joined region 28 is determined, among the echo levels for each scanning position obtained in the step a2, by using the joined region estimation unit 37. For example, the reference echo level H0 is obtained as an average of the echo levels obtained during the scanning operation over the non-joined region 28. Once the joined region estimation unit 37 has determined the reference echo level H0, the procedure goes to a step a4.

In the step a4, the joined region estimation unit 37 determines the level threshold value C1 based on the function of the variables, i.e., the reference echo level H0 and the plate thickness t1 of the upper plate 22. Once the level threshold value C1 has been determined, the two scanning position P1, P2 that correspond to the echo level coincident with the level threshold value C1 are extracted, respectively. Thereafter, the length of the line connecting the two scanning positions P1, P2 is estimated as the diametric size L of the joined region 21, and then the procedure goes to a step a5.

In the step a5, if the estimation of the joining strength is determined to be performed, the procedure goes to a step a6, while if it is not determined to be performed, the procedure goes to a step a7. For instance, in the case of estimating the joining strength, a joining strength estimation command is introduced, in advance, due to the input unit 41. Then, when the processor circuit 43 judges that the strength estimation command has been introduced, the procedure goes to the step a6, while if not so, the procedure goes to the step a7.

In the step a6, the joining strength estimation unit 38 estimates the joining strength, based on the diametric size L of the estimated joined region 21 as well as on the relational expression or data base for obtaining the joining strength provided in advance. As shown in FIG. 9, since the diametric size L of the estimated joined region 21 and the joining strength have a one-to-one relationship relative to each other, the joining strength can be estimated, based on the relationship, without destroying the joined object 20. In such a manner, once the joining strength has been estimated, the estimation result is displayed on the display 40, and then the procedure goes to a step a7. In the step a7, the estimation operation for the joining strength is ended. In this embodiment, although the estimation procedure includes the step of estimating the joining strength, the estimation work may be ended when the step of estimating the diametric size L of the joined region 21 is ended, without estimating the joining strength. Alternatively, the estimation result obtained by the joined region estimation unit 37 may be displayed on the display 40.

As described above, according to this embodiment, the joined region 21 can be estimated, based on the observed reflected wave of the ultrasonic wave, by introducing the ultrasonic wave into the joined object 20 from the backing face 25 opposed to the joining tool plunging face 24. Consequently, the joined region 21 and the joining strength can be reliably estimated, without being affected by the unevenness or concave/convex shape formed in the joining tool plunging face 24, that is, even in the case in which the thickness of the joined object 20 is changed by the joining mark 29.

In this manner, by estimating the joined region 21 by using the ultrasonic wave, the quality of joining and the joining strength can be estimated, without destroying the joined object 20, as such significantly reducing the cost required for the quality inspection as compared with the case requiring the destructive inspection. Besides, even in the case of a large-size joined object for which the destructive inspection is usually difficult, the joining quality and the joining strength can be estimated.

For instance, in the case in which the time required for plunging the joining tool is relatively short, or the like case, the size of the joined region 21 is not consistent even under the same joining conditions, causing variation in the joining strength. Even in such a case, according to this embodiment, the joining strength can be estimated by using the ultrasonic wave, without destroying the joined object 20. Accordingly, the time and labor required for preparing the joined object for use in the destructive inspection and the time and labor for performing the destructive inspection can be saved, thereby enhancing the working efficiency. Additionally, even after producing products each including the joined object 20, the quality inspection for estimating the joining strength of the joined object 20 can be performed, without destroying each product.

Furthermore, according to this embodiment, by scanning the ultrasonic probe 31, each position over the boundary of the joined region 21 and the non-joined region 28 can be estimated as well as a general size of the joined region 21 can be estimated. Thus, information necessary for works for obtaining the joining strength as well as for inspecting the quality of joining can be obtained.

Moreover, the level threshold value C1 as the boundary condition can be determined based on the observed reflected wave in the case in which the ultrasonic wave incident position is located over the non-joined region 28. Consequently, the boundary condition can be determined for each joined object 20. Thus, even in the case in which the boundary condition varies with each joined object 20, the joined region 21 can be precisely estimated. In addition, since the joined region 21 is estimated based on the echo level, i.e., the amplitude of the observed reflected wave, there is no need for analyzing frequencies of wave forms included in the reflected wave, significantly facilitating the estimation for the joined region 21. Besides, since the reference echo level can be obtained when the ultrasonic probe is scanned over the non-joined region 28, the working accuracy and efficiency can be enhanced.

While, in this embodiment, the joined region 21 is estimated based on the echo level of the observed reflected wave, the estimation is not limited to this aspect. For instance, the joined region 21 may also be estimated from the scanning position when another feature than the echo level of the observed reflected wave satisfies the predetermined boundary condition. For example, as in a third embodiment described below, the joined region 21 may be estimated based on a feature related to the frequency of the observed reflected wave.

While, in the embodiment described above, the estimation method and the estimation apparatus for estimating the joined region 21 and the joining strength of the joined object have been shown and discussed, a testing method employing such an estimation method is also included in the present invention. Namely, this testing method is designed to inspect the joined object based on the estimation result obtained by the estimation method. For example, in the case in which the size of the estimated joined region 21 or joining strength is greater than a predetermined acceptable value, the object can be inspected or judged as one satisfying the required joining quality. In this manner, by inspecting each joined object by using the aforementioned estimation method, the joined object can be inspected in a non-destructive manner, thereby enhancing the working efficiency. For example, the so-called one hundred percent inspection can be performed for the joined objects, as such correctly eliminating incompletely joined products.

Furthermore, a testing apparatus adapted to inspect the joined object described above is also included in the present invention. In addition to the construction of the estimation apparatus shown in FIG. 2, the testing apparatus further includes a judging unit or judging means adapted for judging whether each joined object is acceptable or not. Namely, the judging unit is adapted to judge whether or not the estimation result obtained due to the estimation means satisfies a predetermined required value. For example, if the size of the joined region 21 or joining strength is judged to be greater than the required value, the quality of the inspected joined object will be judged to satisfy a predetermined quality. In this case, this judgment result is displayed on the display 40. The judging unit can be achieved by performing operating programs stored in a preset memory circuit, by using the processor circuit 43. The judging unit is configured to compare an introduced acceptable value with an estimated value when an acceptable diameter, acceptable area or acceptable strength of the joined region 21 is introduced as the introduced value by the input unit.

Figure 11:
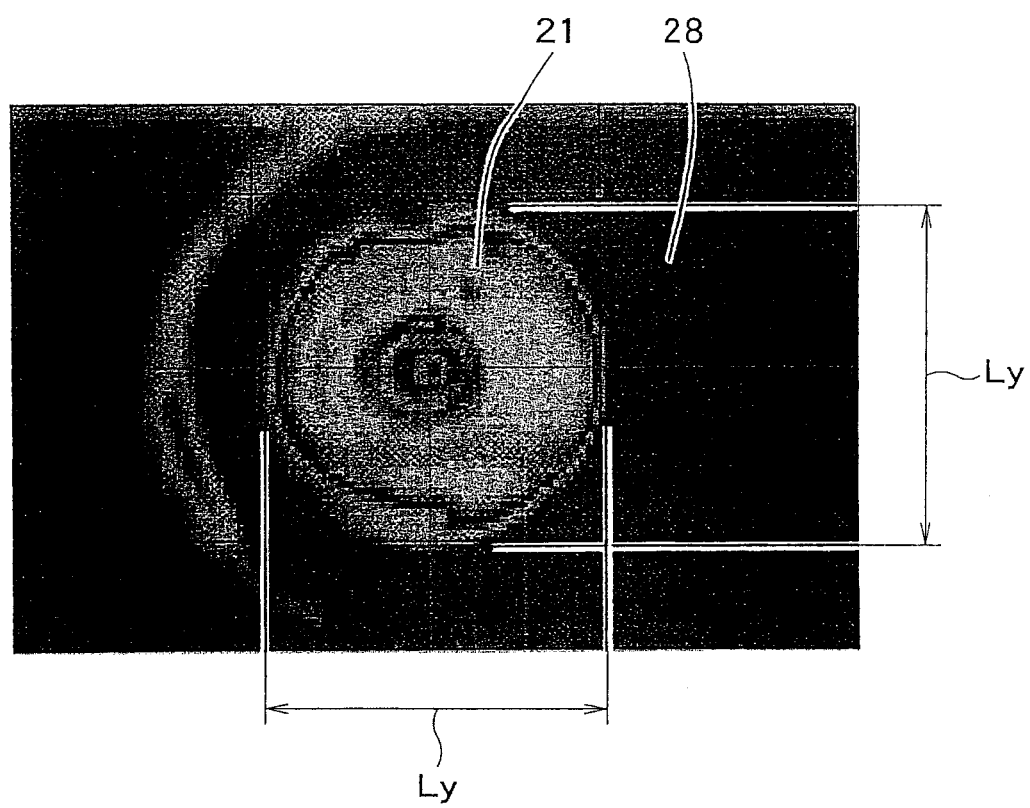
FIG. 11 is a plan view showing an estimation result for illustrating the estimation method for the joined object, this method being a second embodiment of the present invention.

FIG. 11 is a plan view showing an estimation result for illustrating the estimation method for the joined object, this method being a second embodiment of the present invention. While the diametric size L has been estimated as the size of the joined region 21 in the first embodiment of this invention, the area is used for estimating the size of the joined region 21 in the second embodiment of this invention. Because the other construction is the same as that of the first embodiment, the same construction will not be detailed below, and like parts will be designated by like reference numerals.

As shown in FIG. 3(2), when the ultrasonic probe 31 is scanned in both of the first scanning direction X and the second scanning direction Y, the joined region estimation unit 37 obtains a diametric size Lx of the joined region 21 estimated in the case in which the ultrasonic probe 31 is scanned in the first scanning direction X and a diametric size Ly of the joined region 21 estimated in the case in which the ultrasonic probe 31 is scanned in the second scanning direction Y, respectively. Thereafter, the joined region estimation unit 37 estimates the area of the joined region 21 as a value obtained by $Lx \cdot Ly \cdot \pi/4$, in which Lx is the diametric size of the joined region 21 in the first scanning direction X and Ly is the diametric size of the joined region 21 in the second scanning direction Y.

Alternatively, as shown in FIG. 3(3), when the ultrasonic probe 31 is scanned over the preset whole two-dimensional surface area including the region spreading over the joined region 21, the joined region estimation unit 37 estimates the area of the joined region 21 as an area obtained by totaling respective regions corresponding to scanning positions each exhibiting the echo level lower than the level threshold value C1. In FIG. 11, regions depicted white correspond to the scanning positions each exhibiting the echo level lower than the level threshold value C1. Thus, the area of the joined region 21 can be estimated as an area obtained by totaling the respective regions depicted white.

Figure 12:
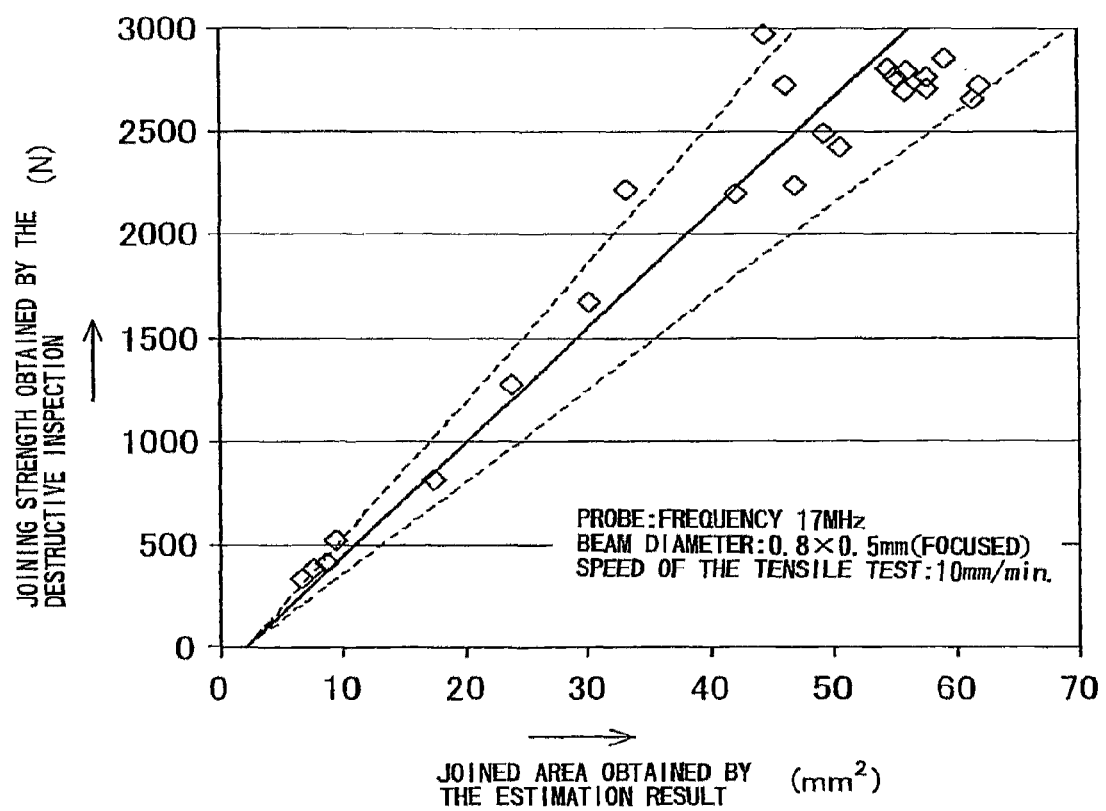
FIG. 12 is a graph for showing distribution of the joining strength of the joined object 20 measured by the destructive inspection, relative to an area of the estimated joined region 21.

FIG. 12 is a graph for showing distribution of the joining strength of the joined object 20 measured by the destructive inspection relative to the area of the estimated joined region 21. In FIG. 12, the joining strength estimated based on an average of the estimated area of the joined region is expressed by a solid line, while the joining strength estimated based on each value obtained by changing ±20% the average value of the estimated area of the joined region is shown by broken lines, respectively. As shown in FIG. 12, it is found that there is a one-to-one mutual relation between the estimated area of the joined region 21 and the joining strength. Accordingly, with preparation of a computing equation or data base expressing the relationship between the area of the joined region 21 estimated in advance and the joining strength, the joining strength can be calculated, by using such a computing equation or data base, based on the estimated joined region 21. For instance, when the estimated area of the joined region 21 is expressed as A, the joining strength will be generally expressed by $K2 \cdot A$. In this case, K2 is a predetermined constant, which can be experimentally obtained.

In such a manner, also in the case of obtaining the area as the size of the joined region 21, the joining strength can be obtained by using the procedure of the estimation method similar to that shown in FIG. 10. In this case, as compared with the case shown in FIG. 10, in the step a4 of estimating the size of the joined region 21, the area of the joined region 21 will be estimated. In addition, in the step a5 of estimating the joining strength, the joining strength estimation unit 38 will estimate the joining strength, based on the estimated area A of the joined region 21 as well as on the preset computing equation or data base for obtaining the joining strength. Because the other steps are similar to those in the procedure shown in FIG. 10, they are not detailed now. In this embodiment, by obtaining the joining strength based on the area of the joined region 21, rather than on the diametric size of the joined region 21, the joining strength can be more precisely estimated, even in the case in which the joined region 21 is formed into a generally elliptic shape.

Figure 13:
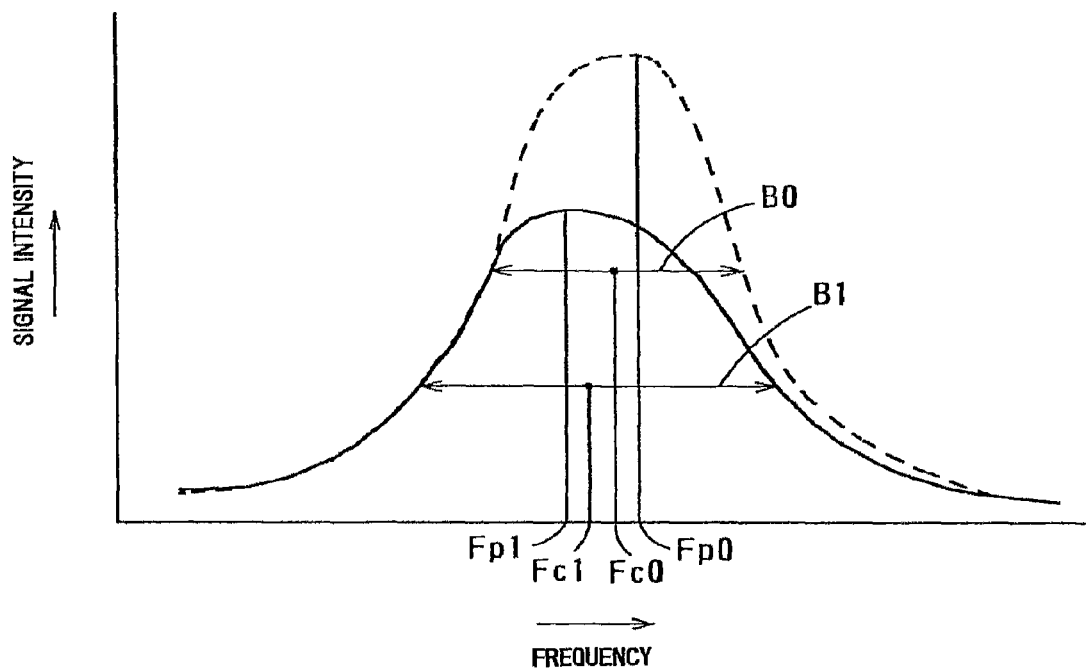
FIG. 13 is a graph for showing a result of a frequency analysis of a wave form included in an observed reflected wave 45.

FIG. 13 is a graph for showing a result of a frequency analysis of a wave form included in the observed reflected wave 45. In this case, the horizontal axis designates frequency distribution of the wave form included in the observed reflected wave. The vertical axis expresses the amplitude for each frequency of the wave form included in the observed reflected wave. Also in FIG. 13, the frequency distribution of the wave form included in the observed reflected wave when the scanning position is located over the non-joined region 28 is shown by a broken line. In addition, the frequency distribution of the wave form included in the observed reflected wave when the scanning position is located over the joined region 21 is shown by a solid line.

When the scanning position is located over the joined region 21, as compared with the case in which it is located over the non-joined region 28, since the interface 27 between the upper plate 22 and the lower plate 23 has disappeared, the ultrasonic wave is more likely to be transmitted from the upper plate 22 to the lower plate 23. Of the wave forms included in the reflected wave, the wave forms in a higher frequency band exhibit higher directivity as compared with the wave forms in a lower frequency band. If the boundary face between the joined region 21 and each of the remaining regions is inclined relative to the backing face 25, the wave forms in the higher frequency band will be taken in, in a lesser amount, as the reflected wave. Besides, the wave forms in the higher frequency band are more likely to be lowered as compared with those in the lower frequency band.

Accordingly, with respect to a peak frequency fp, a frequency of the wave form exhibiting the maximum amplitude value in the frequency distribution band of the wave form included in the observed reflected wave, a peak frequency fp1 when the scanning position is located over the joined region 21 is lower than a peak frequency fp0 when the scanning position is located over the non-joined region 28. With respect to a central frequency fc, a frequency positioned at the center of the frequency distribution band lower by a predetermined amount than the maximum frequency value in the frequency distribution band of the wave form included in the observed reflected wave, a central frequency fc1 when the scanning position is located over the joined region 21 is lower than a central frequency fc0 when the scanning position is located over the non-joined region 28. In this embodiment, the amplitude value lower by the predetermined amount than the maximum amplitude value is set lower by a predetermined rate, for example 6 dB, as compared with the amplitude value of the wave form of the peak frequency fp.

In addition, with respect to an observed frequency bandwidth B of a wave form higher than an amplitude value lower by a predetermined amount than the maximum amplitude value in the frequency distribution band of the wave form included in the observed reflected wave, an observed frequency bandwidth B1 when the scanning position is located over the joined region 21 is greater than an observed frequency bandwidth B0 when the scanning position is located over the non-joined region 28. In this embodiment, the amplitude value lower by the predetermined amount than the maximum amplitude value is set lower by a predetermined rate, for example 6 dB, as compared with the amplitude value of the wave form of the peak frequency fp.

Figure 14:
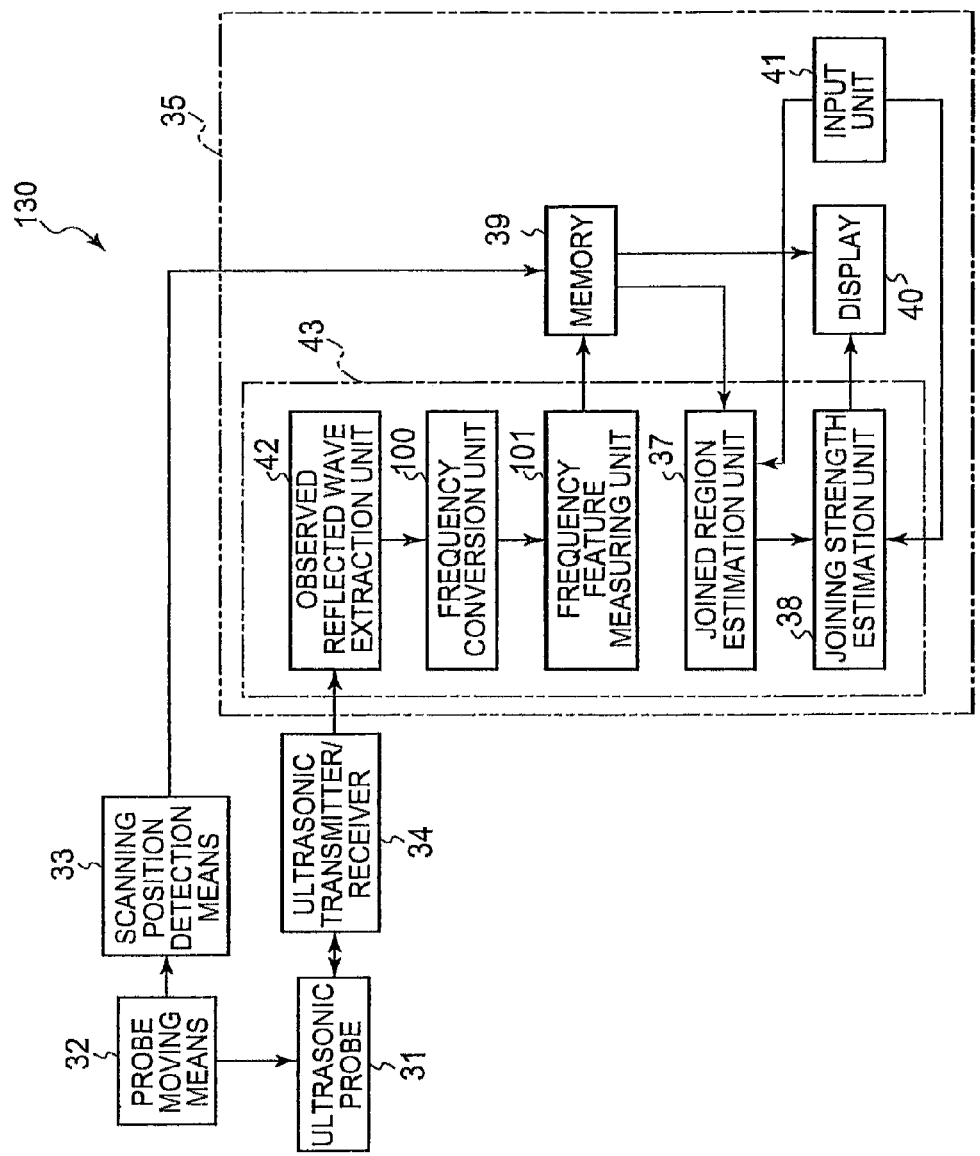
FIG. 14 is a block diagram showing an estimation apparatus 130 of a third embodiment of the present invention.

FIG. 14 is a block diagram showing the estimation apparatus 130 of the third embodiment of the present invention. The estimation apparatus 130 of the third embodiment of this invention has a construction similar to that of the estimation apparatus 30 of the first embodiment. Thus, the same construction as in the first embodiment will not be detailed below, and like parts will be designated by like reference numerals.

The estimation apparatus 130 of the third embodiment includes a frequency feature measuring unit 101 provided in place of the echo level measuring unit 36 of the estimation apparatus 30 of the first embodiment. In addition, the estimation apparatus 130 further includes a frequency conversion unit 100. The frequency conversion unit 100 is configured to analyze the frequency of the wave form included in the observed reflected wave extracted by the observed wave form extraction unit 42 and separate the wave form included in the observed reflected wave into each frequency component. The frequency conversion unit 100 provides the result of frequency analysis to the frequency feature measuring unit 101. The frequency feature measuring unit 101 is configured to measure an amount of a feature required for estimating the joined region 21, for each scanning position of the ultrasonic probe 31, from the result of frequency analysis and then provide the result of measurement, in succession, to the memory 39 in order to store it therein. The frequency conversion unit 100 and frequency feature measuring unit 101 can be achieved by performing operating programs stored in a preset memory circuit by employing a processor circuit 43. Consequently, the joined region estimation unit 37 reads the information stored in the memory 39 by the frequency feature measuring unit 101 and estimates the scanning position corresponding to the frequency feature satisfying the predetermined boundary condition, as a position over the joined region 21. The other construction is similar to that of the estimation apparatus 30 of the first embodiment shown in FIG. 2.

Figure 15:
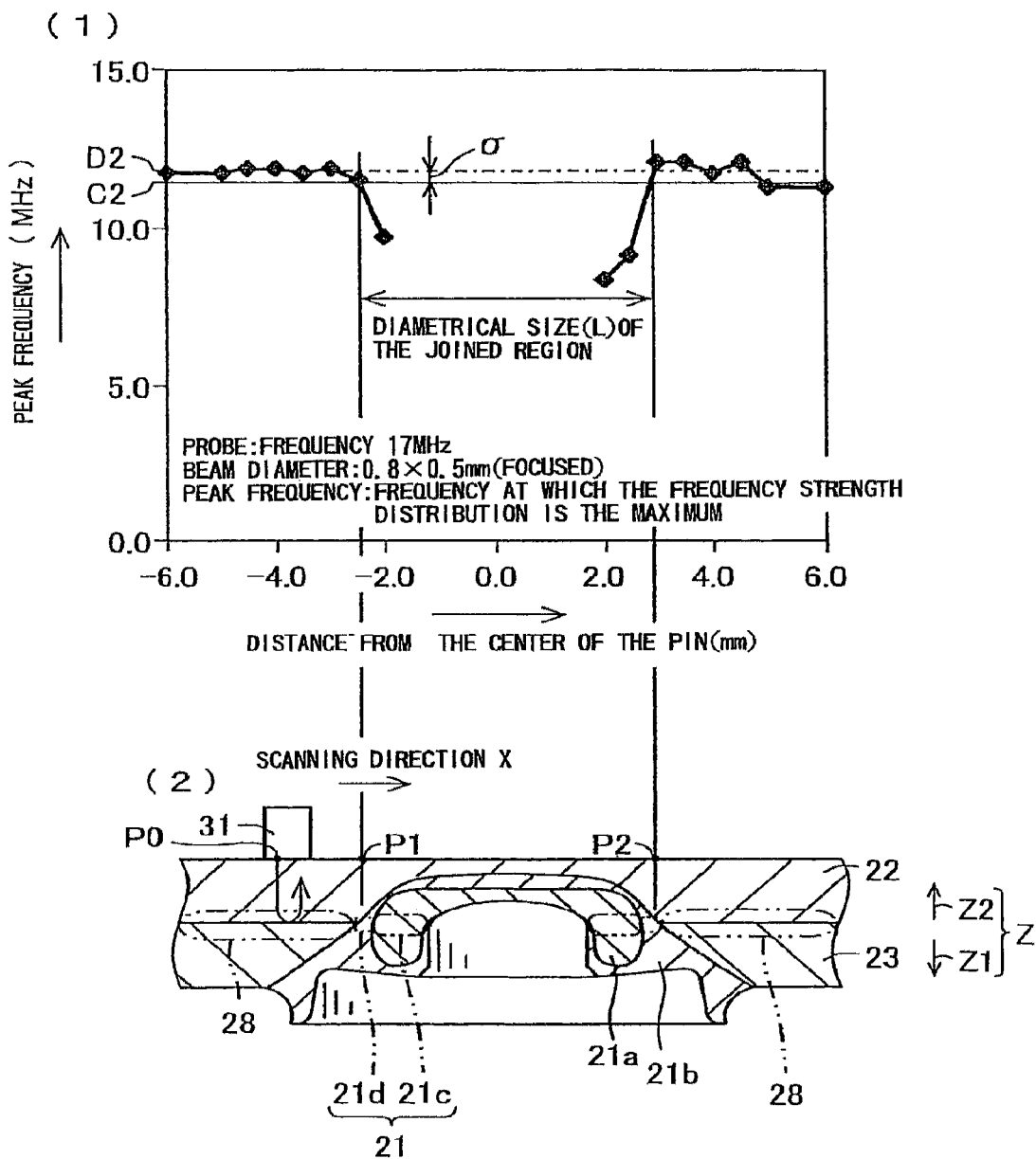
FIG. 15 is a diagram for illustrating changes of a peak frequency, relative to the changes of the scanning position.

FIG. 15 is a diagram for illustrating changes of the peak frequency relative to the changes of the scanning position. FIG. 15(1) is a graph illustrating the changes of the peak frequency relative to the changes of the scanning position, and FIG. 15(2) is a section of the joined object corresponding to the graph of FIG. 15(1). In FIG. 15(1), the scanning position is expressed on the horizontal axis, while the peak frequency is designated on the vertical axis. In the case in which the ultrasonic probe 31 is scanned in the scanning direction such that it can pass through the center of the joining mark 29 as shown in FIG. 3(1), the scanning position, in which the peak frequency fp of each scanning position is lower than a preset peak frequency threshold value C2, can be estimated as a position over the joined region 21, as shown in FIG. 15(1). The peak frequency threshold value C2 is used as a reference of the boundary condition for judging whether or not the scanning position is located over the joining region 21, and is set lower than the peak frequency fp0 of the observed reflected wave in the case in which the ultrasonic wave incident position is located over the non-joined region 28.

In addition, the scanning position P1 in which the peak frequency fp of each scanning position is switched from a state higher than the peak frequency threshold value C2 to a state lower than the same threshold value C2 and the scanning position P2 in which the peak frequency is switched from the state lower than the peak frequency threshold value C2 to the state higher than the same threshold value C2 can be estimated as positions over the boundary between the joined region 21 and the non-joined region 28, respectively. Furthermore, the length of the line connecting the two scanning positions P1, P2 over the respective boundary positions can be estimated as the diametric size of the joined region 21.

In this embodiment, the peak frequency threshold value C2, as the boundary condition, is determined based on the peak frequency fp0 of the observed reflected wave in the case in which the ultrasonic wave incident position is located over the non-joined region 28. More specifically, the peak frequency threshold value C2 is set at a frequency lower than an average D2 of the reference peak frequency fp0, by a value greater than a standard deviation $\sigma$ of the reference peak frequency fp0, wherein the standard deviation $\sigma$ is calculated from the reference peak frequency fp0 of the non-joined region 28.

The reference peak frequency fp0 corresponds to a frequency of the wave form at which the amplitude becomes the maximum, among the wave forms analyzed for each frequency distribution of the observed reflected wave. The average D2 and the standard deviation $\sigma$ of the reference peak frequency fp0 may be measured in advance, or otherwise calculated based on information provided from the frequency conversion unit 100 prior to measurement of the frequency feature due to the frequency feature measuring unit 43. In this case, the frequency feature measuring unit 101 measures the peak frequency fp of the observed reflected wave. The joined region estimation unit 37 serves to estimate the scanning position, in which the peak frequency fp of each scanning position is lower than the predetermined peak frequency threshold value C2, as a position over the joined region 21.

Similarly, also in the case of using the central frequency fc in place of the peak frequency fp, the joined region 21 can be estimated. More specifically, in the case of scanning the ultrasonic probe 31 in the scanning direction such that it can pass through the center of the joining mark 29 as shown in FIG. 3(1), the scanning position, in which the central frequency fc of each scanning position is lower than a predetermined central frequency threshold value, can be estimated as a position over the joined region 21. The central frequency threshold value is used as a reference of the boundary condition for judging whether or not the scanning position is located over the joining region 21, and is set lower than the central frequency fc0 of the observed reflected wave in the case in which the ultrasonic wave incident position is located over the non-joined region 28.

In addition, the scanning position P1 in which the central frequency fc of each scanning position is switched from a state higher than the central frequency threshold value to a state lower than the same threshold value and the scanning position P2 in which the central frequency is switched from the state lower than the central frequency threshold value to the state higher than the same threshold value can be estimated as positions over the boundary between the joined region 21 and the non-joined region 28, respectively. Furthermore, the length of the line connecting the two scanning positions P1, P2 over the respective boundary positions can be estimated as the diametric size of the joined region 21.

In this embodiment, the central frequency threshold value as the boundary condition is determined based on the observed reflected wave in the case in which the ultrasonic wave incident position is located over the non-joined region 28. More specifically, the central frequency threshold value is set at a frequency lower than an average of the reference central frequency fc0, by a value greater than a standard deviation σ set for the reference central frequency fc0.

The reference central frequency fc0 corresponds to a frequency as the centre of the frequency bandwidth between the highest frequency and the lowest frequency of the wave forms having amplitudes greater than a predetermined value, among the wave forms analyzed for each frequency distribution of the observed reflected wave. The average and the standard deviation σ of the reference central frequency fc0 may be measured in advance, or otherwise calculated based on information provided from the frequency conversion unit 100 prior to the measurement of the frequency feature by the frequency feature measuring unit 43. In this case, the frequency feature measuring unit 101 measures the central frequency fc of the observed reflected wave. The joined region estimation unit 37 serves to estimate the scanning position, in which the central frequency fc of each scanning position is lower than the predetermined central frequency threshold value, as a position over the joined region 21.

Figure 16:
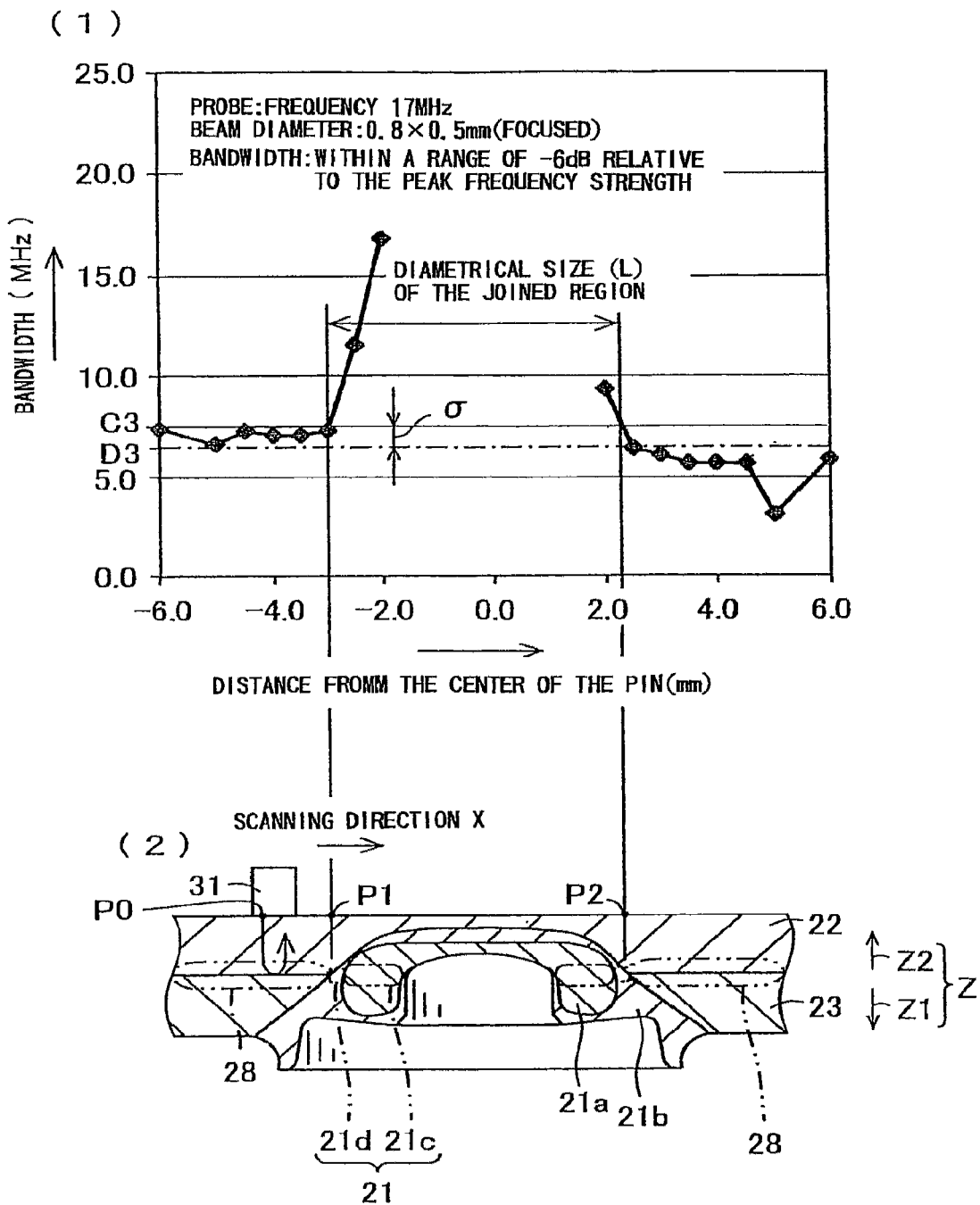
FIG. 16 is a diagram for illustrating changes of a bandwidth, relative to the changes of the scanning position.

FIG. 16 is a diagram for illustrating changes of the bandwidth relative to changes of the scanning position. FIG. 16(1) is a graph illustrating the changes of the bandwidth relative to the changes of the scanning position, and FIG. 16(2) is a section of the joined object corresponding to the graph of FIG. 16(1). In FIG. 16(1), the scanning position is expressed on the horizontal axis, while the bandwidth is designated on the vertical axis. In the case in which the ultrasonic probe 31 is scanned in the scanning direction such that it can pass through the center of the joining mark 29 as shown in FIG. 3(1), the scanning position, in which the observed bandwidth B of each scanning position is lower than a predetermined bandwidth threshold value C3, can be estimated as a position over the joined region 21, as shown in FIG. 16(1). The bandwidth threshold value C3 is used as a reference of the boundary condition for judging whether or not the scanning position is located over the joining region 21, and is set wider than the observed bandwidth B0 of the observed reflected wave in the case in which the ultrasonic wave incident position is located over the non-joined region 28.

The scanning position P1 in which the observed bandwidth B of each scanning position is switched from a state narrower than the bandwidth threshold value C3 to a state wider than the same threshold value C3 and the scanning position P2 in which the observed bandwidth B is switched from the state lower than the bandwidth threshold value C3 to the state higher than the same threshold value C3 can be estimated as positions over the boundary between the joined region 21 and the non-joined region 28, respectively. Furthermore, the length of the line connecting the two scanning positions P1, P2 over the respective boundary positions can be estimated as the diametric size of the joined region 21.

In this embodiment, the bandwidth threshold value C3 as the boundary condition is determined based on the observed reflected wave in the case in which the ultrasonic wave incident position is located over the non-joined region 28. For instance, the bandwidth threshold value C3 is set at a bandwidth greater than an average D3 of the reference bandwidth B0, by a value greater than a standard deviation σ of the bandwidth, wherein the standard deviation σ is calculated from the bandwidth of the non-joined region 28. Alternatively, for instance, the bandwidth threshold value C3 is set at a bandwidth wider than the reference bandwidth B0 by a preset amount. As one example, it is set at a bandwidth wider than the reference bandwidth B0 by approximately 1.2 MHz. In this case, the reference bandwidth B0 corresponds to a frequency bandwidth of the wave form greater than amplitude lowered, by a preset amount, for example 6 dB, from amplitude of the wave form of the reference peak frequency fp0.

The observed bandwidth B corresponds to a frequency bandwidth of the wave form greater than amplitude lowered, by the preset amount, for example 6 dB, from amplitude of the wave form of the corresponding peak frequency fp1. The reference bandwidth B0 may be set in advance, or otherwise calculated based on information provided from the frequency conversion unit 100 prior to the measurement of the frequency feature by the frequency feature measuring unit 43.

For example, the frequency feature measuring unit 101 measures the observed bandwidth B of the observed reflected wave. In this case, the joined region estimation unit 37 serves to estimate the scanning position, in which the observed bandwidth B of each scanning position is wider than the predetermined bandwidth threshold value C3, as a position over the joined region 21.

As described above, in the third embodiment, the joined region 21 is estimated based on the frequency feature of the observed reflected wave, rather than on the echo level H. As discussed above, the frequency feature may be either one of the peak frequency fp, central frequency fc and observed bandwidth B. Furthermore, the joined region 21 may be estimated based on the other frequency features of the observed reflected wave. In the third embodiment, although only the boundary condition for estimating the joined region 21 is different from the first embodiment, the method for estimating the joining strength can be performed in the same manner as in the first embodiment. Other than estimating the diametric size of the joined region 21 as with the case of the second embodiment, the joining strength may be estimated by obtaining the area of the joined region 21. Also in the third embodiment, the same effect as that of the first embodiment can be obtained.

Due to the frequency analysis, even in the case in which the echo level is considerably low or in the case in which noise is conspicuous, the joined area 21 and the joining strength can be precisely estimated. Besides, due to a significantly greater change that can be measured between the joined region 21 and the non-joined region 28, the joined area 21 and the joining strength can be estimated with higher precision. The influence of the noise may be further reduced by providing a filter for cutting unwanted or undesired frequencies.

Due to the estimation of the joined region 21 based on the peak frequency fp or frequency bandwidth B, the joined region 21 can be estimated, even in the case in which the frequency distribution of each wave form included in the observed reflected wave is shifted to some extent from a normal distribution. Furthermore, with the determination of the boundary condition for estimating the joined region 21 based on the standard deviation σ of the peak frequency fp and/or central frequency fc, there is no need for setting an additional parameter, for example, the plate thickness of the upper plate 22 or the like, for each joined object 20, as such facilitating the determination of the boundary condition.

Figure 17:
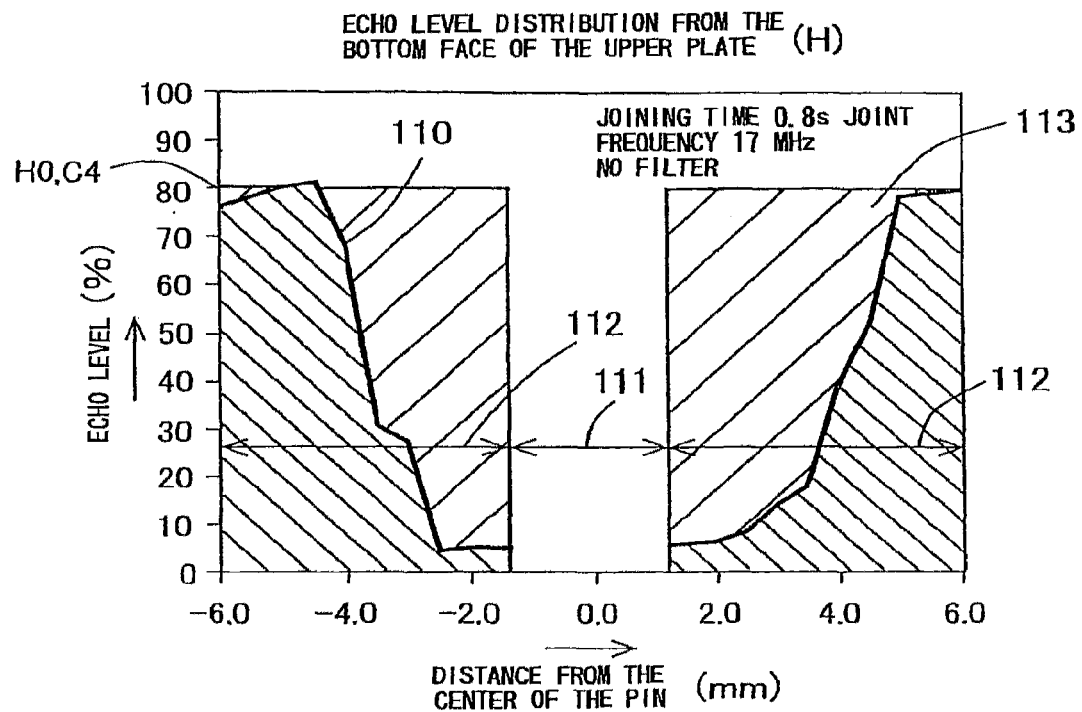
FIG. 17 is a graph for illustrating the estimation method of a fourth embodiment of the present invention.

FIG. 17 is a graph for illustrating the estimation method of a fourth embodiment of the present invention. In FIG. 17, the scanning position is expressed on the horizontal axis, while the echo level is designated on the vertical axis. More specifically, in FIG. 17, a percentage of the echo level for each scanning position relative to the reference echo level H0 is expressed on the vertical axis.

In the first and second embodiments of the present invention, the size of the joined region 21 is first obtained, and the joining strength is then obtained based on the size. However, in the fourth embodiment of this invention, without obtaining the size of the joined region 21, the joining strength is directly estimated based on the echo level extracted from the observed reflected wave. In the fourth embodiment, the computing procedure of the joined region estimation unit 37 is different from that of the first embodiment. However, since the other construction is substantially the same as that of the first embodiment, it will not be detailed below.

In the fourth embodiment, an area 113 is obtained by integrating a distance or difference between an echo level 110 of each scanning position and a preset echo level C4 along a range or interval 112 of the scanning position except for a scanning position 111 in which the pin portion was plunged. In this embodiment, the reference echo level H0 is set as the preset echo level C4.

In this case, with decrease of the reflected wave reflected from the interface 27 between the upper plate 22 and the lower plate 23, the echo level is also deceased. Namely, increase of the area 113 means increase of disappearance of the interface 27, i.e., increase of the joining strength. Accordingly, the area 113 has a one-to-one relationship with the joining strength. Thus, based on such a relationship, the joining strength estimation unit 38 can estimate the joining strength. While, in this embodiment, changes of the echo level is integrated, the joining strength may be directly determined, based on an integrated value of changes of other features of the observed reflected wave, including the aforementioned peak frequency fp, central frequency fc, preset bandwidth B and the like. Also in such a case, the joining strength can be directly determined, based on the integrated value obtained by integrating each changing amount of the feature's value along the interval 112 of the scanning position except for the scanning position 111 in which the pin portion was plunged.

Alternatively, the joined region estimation unit 38 may obtain the position of the joined region 21 based on a changing amount of the observed reflected wave relative to the change of the scanning position. For instance, in the case in which the changing amount of the feature's value of the observed reflected wave relative to the change of the scanning position is relatively steep, the scanning position corresponding to such a steep change may be estimated as a position located over the boundary position between the stir-joined region 21c and the pressure-joined region 21d. Alternatively, the scanning position, in which an inclination of a change of the feature's value of the observed reflected wave, or a value obtained by differentiating the change of the feature's value becomes greater than a predetermined value, may be estimated as a position located over the boundary position between the stir-joined region 21c and the pressure-joined region 21d. In this way, by obtaining the shapes of the stir-joined region 21c and pressure-joined region 21d and adding the result to the estimation of the joining strength, further accurate joining strength can be obtained.

In such a manner, the joining strength of the joined object may be estimated, based on an integrated feature's value of the observed reflected wave along a unit range including a region located over the joined region 21 as well as on a relation of conversion which is set for converting the feature's value into the strength of the joined object, after taking in the reflected wave of the ultrasonic wave over the unit range. If the incident region of the ultrasonic wave is limited to a unit range, the integrated feature's value will be a value of a feature of the observed reflected wave taken in from the unit range.

Figure 18:
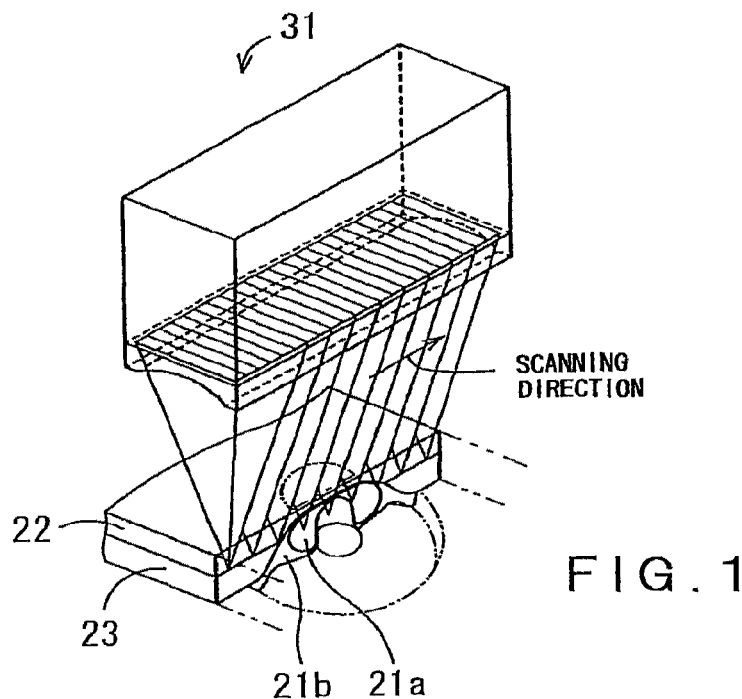
FIG. 18 is a perspective view showing one example of the ultrasonic probe 31 used in the first to fourth embodiments.

FIG. 18 is a perspective view showing one example of the ultrasonic probe 31 used in the first to fourth embodiments. In these embodiments, a phased array ultrasonic probe of a one-dimensional array oscillator type is used as the ultrasonic probe 31. The phased array ultrasonic probe 31 is an array-type probe in which microscopic oscillators are arranged in large numbers, and is adapted to shift timing of the ultrasonic wave generated from each oscillator by changing timing of a pulse applied to each oscillator, as such optionally changing a focusing position of the ultrasonic wave. Thus, there is no need for scanning the ultrasonic probe in the respective array directions, thereby enhancing the working efficiency.

Alternatively, a phased array ultrasonic probe of a two-dimensional array oscillator type can also be used. In addition, the ultrasonic probe 31 of a single-probe type can also be employed. Alternatively, the ultrasonic probe of a two-probe type composed of a probe adapted for generating the ultrasonic wave and a probe adapted for taking in the ultrasonic wave may also be used. Rather than using a point-focusing type probe, a non-focusing type probe can also be used. Alternatively, rather than introducing or radiating the ultrasonic wave vertically to the backing face 25, the ultrasonic wave may be introduced obliquely to the backing face 25.

Figure 19:
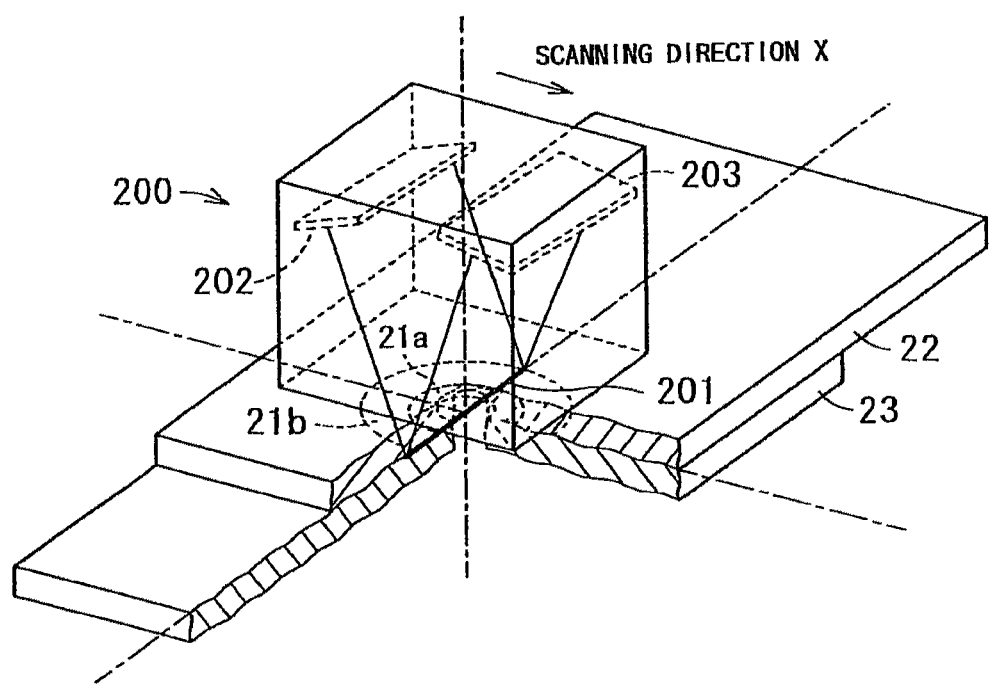
FIG. 19 is a perspective view showing an ultrasonic probe 200 related to a fifth embodiment of the present invention.
Figure 20:
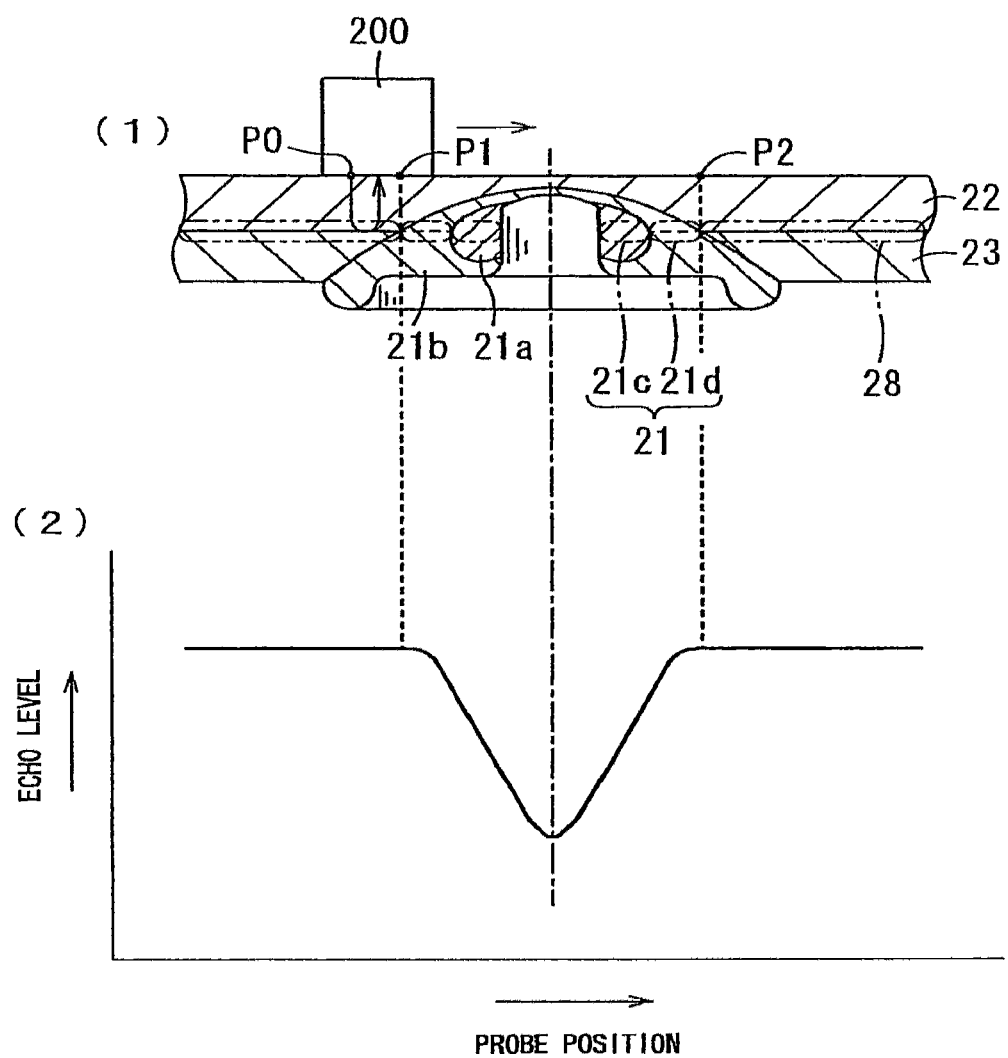
FIG. 20 is a diagram showing a relationship between the scanning position and the echo level.

FIG. 19 is a perspective view showing an ultrasonic probe 200 related to a fifth embodiment of the present invention. FIG. 20 is a diagram showing a relationship between the scanning position and the echo level. FIG. 20(2) is a graph showing changes of the echo level relative to changes of the scanning position, and FIG. 20(1) is a section corresponding to the graph of FIG. 20(2). In the fifth embodiment of this invention, the construction of the ultrasonic probe 200 is different from that of the first embodiment. In addition, the joined region estimation unit 37 is eliminated, and the joining strength estimation unit 38 is configured to directly estimate the joining strength based on the echo level. Because the remaining construction is the same as that of the previous embodiment, it will not be detailed below.

The ultrasonic probe 200 is achieved by a linear focusing type probe. In the ultrasonic probe 200, a linear ultrasonic wave introducing region 201 having a length longer than the diametric size of the joined region 21 is formed and a transmitter oscillator 202 and a receiver oscillator 203 are provided separately. The ultrasonic probe 200 of this embodiment has an oscillator size of 10×2 mm, and generates an ultrasonic wave having a frequency of 10 MHz. In this case, the echo level measuring unit 36 measures an integrated echo level of the observed reflected wave reflected in the vicinity of a position along the reference direction corresponding to the interface 27 between the upper plate 22 and the lower plate 23.

By using such an ultrasonic probe 200, as shown in FIG. 19, the integrated echo level, when the ultrasonic wave introducing region 201 is located such that it can pass through over the center of the joining mark 29, is obtained. In other words, as shown in FIG. 20, by scanning the ultrasonic probe 200, the ultrasonic scanning position in which the integrated echo level becomes the minimum is searched.

Figure 21:
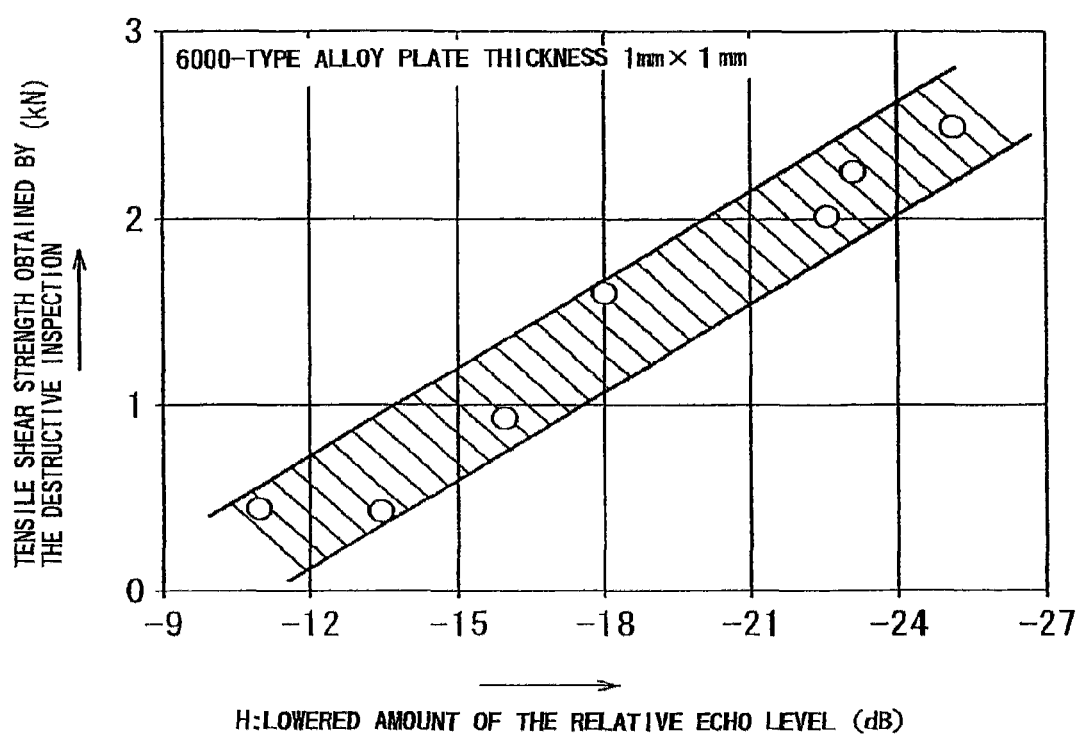
FIG. 21 is a graph showing a relationship between a relative echo level and the area of the joined region 21.

FIG. 21 is a graph showing a relationship between tensile shear strength and a lowering amount of a relative echo level. In FIG. 21, a rate of an integrated minimum echo level, at which the echo level is the minimum, relative to an integrated reference echo level in the case in which the ultrasonic wave is introduced into the non-joined region 28, is shown as the lowering amount of the relative echo level. In FIG. 21, a lowering amount of the relative echo level is expressed on the horizontal axis, while the tensile shear strength of the joined object obtained by a destructive inspection is designated on the vertical axis. As shown in FIG. 21, the lowering amount of the relative echo level has a substantially one-to-one relationship with the joining strength. Accordingly, if the integrated minimum echo level is obtained in advance, the joining strength can be directly estimated by substituting the obtained integrated minimum echo level into a relational equation for calculating the joining strength. This relational equation can be obtained in advance by an experiment or the like.

In this manner, the joining strength estimation unit 38 can directly estimate the joining strength based on the integrated minimum echo level. While, in this embodiment, the ultrasonic probe is achieved by using the linear focusing probe, a similar effect can also be obtained by employing a non-focusing type ultrasonic probe. In such a case, it is preferred that an area of the ultrasonic wave introducing region of the non-focusing type ultrasonic probe is sufficiently larger than the area of the joined region 21.

In this embodiment, the joining strength of the joined object can be estimated, based on an integrated feature's value of the observed reflected wave along a unit range including a region located over the joined region 21 of the joined object 20 as well as on a relation of conversion which is set for converting the feature's values into the strength of the joined object, after introducing the ultrasonic wave into the joined object from the backing face 25 of the joined object 20 while taking in the reflected wave of the ultrasonic wave introduced into the joined object over the unit range. Consequently, there is no need for estimating the size of the joined region 21, thereby facilitating the estimation of the joining strength of the joined object 20.

In the case of using the linear focusing type probe, the ultrasonic probe may be scanned in one direction. Alternatively, in the case of using the non-focusing type probe, the ultrasonic probe may not be scanned. Consequently, the estimation apparatus can be simplified, thus facilitating the estimation of the joining strength. In addition, the integrated feature's value of the observed reflected wave in the unit range may be obtained by scanning the focusing type probe over the unit range as described above. In this case, the integrated feature's value means a value obtained by adding together the feature's values of the observed reflected wave for each scanning position in the unit range or an average value of the feature's values of the observed reflected wave for each scanning position in the unit range. While, in this embodiment, the joining strength is obtained based on the integrated changing amount of the echo level along the unit range, the scanning strength may be directly determined based on changes of other features of the observed reflected wave, including the aforementioned peak frequency fp, central frequency fc, preset bandwidth B and the like.

As stated above, the aforementioned estimation method of the joined region 21 and/or joining strength was described only by way of example, but may be modified without departing from the scope of this invention. For example, in each embodiment, the joined region 21 may be estimated by employing other features of the observed reflected wave than those described above. Alternatively, the joined region 21 may be estimated by combining together the aforementioned features of the observed reflected wave. For instance, to enhance a factor of safety, the minimum value of the joining strength estimated by two or more of the estimation methods described above may be employed as the estimated joining strength. While the ultrasonic probe is scanned in the embodiment described above, the operation is not limited to this aspect. For instance, in the case of estimating whether or not the ultrasonic wave incident position is over the joined region 21, the ultrasonic probe may also be spotted.

While, in the embodiment above, the boundary condition of the observed reflected wave for estimating the joined region 21 is determined based on the observed reflected wave in the case in which the ultrasonic wave incident position is located over the non-joined region 28, the determination of the boundary condition is not limited to this aspect. For example, the boundary condition may be set at a constant value. While, in the embodiment above, the joined region 21 and/or joining strength is estimated in accordance with a computing equation, the joined region 21 and/or joining strength may be estimated by using a data base in place of the computing equation.

Figure 22:
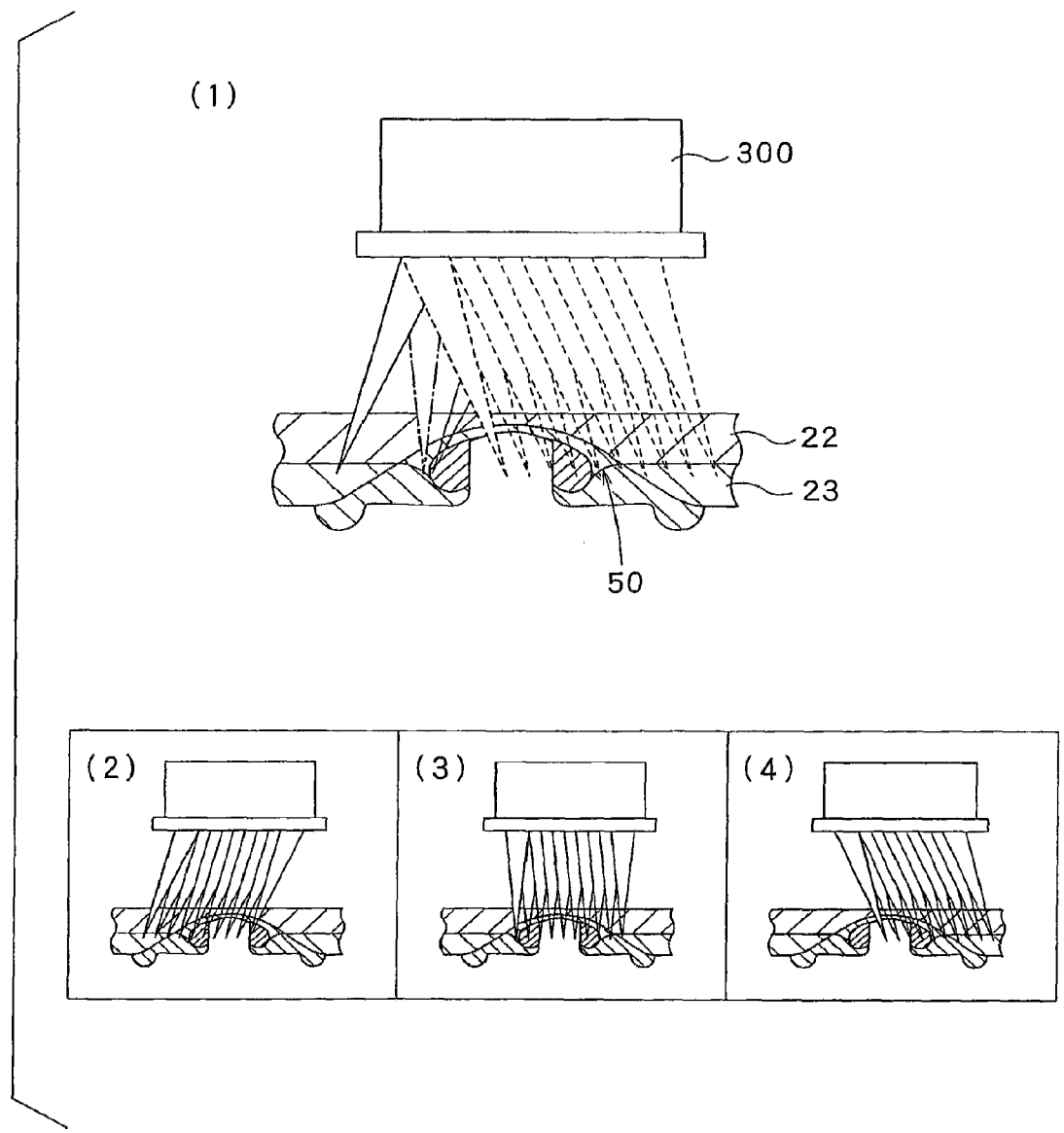
FIG. 22 is a diagram for illustrating a measuring method employing the ultrasonic probe 300, this method being one modification for each embodiment.

As one modification, in the step of measuring the reflected wave in each of the above embodiments, as shown in FIGS. 22(1) to 22(4), the ultrasonic wave may be introduced into the joined object at a plurality of different angles of refraction from the ultrasonic probe 300. This method is effective in particular in the case in which a hooking phenomenon occurs in the joined portion upon the friction stir joining process. The hooking phenomenon means that the joining members 22, 23 are softened upon the friction stir joining process, and the interface between the joining member 22 and the joining member 23 is drawn toward the tool plunging face 24, as such forming a curved portion (or hooking portion) 50 as shown in FIG. 22(1).

Such a hooking portion 50 does not substantially contribute to the joining strength between the joining member 22 and the joining member 23. A degree of generation of such a hooking phenomenon depends on the conditions of the friction stir joining process, including materials of the joining members and the like.

Due to the introduction of the ultrasonic wave from the ultrasonic probe 300 into the joined object 20 with the plurality of different angles of refraction employed in the step of measuring the reflected wave, a reflected echo from the hooking portion 50 can be caught by an angle beam method, even in the case in which the hooking portion 50 exists in the joined object 20. Namely, if the angle of refraction is only 0° (i.e., in the case of vertical injection), the reflected echo from the curved hooking portion 50 can not be caught. Therefore, the hooking portion 50 that does not substantially contribute to the joining strength can not be distinguished from another portion that contributes to the joining strength, thus evaluating the joining strength of the joined object 20 unduly higher than an actual value.

However, in the aforementioned example of this invention, by employing the angle beam method of the angle of refraction of, for example, 20° or 30°, the reflected wave from the hooking portion 50 can be caught. Thus, the joining strength can be precisely estimated even in the case in which the hooking portion 50 exists in the joined object 20.

Figure 23:
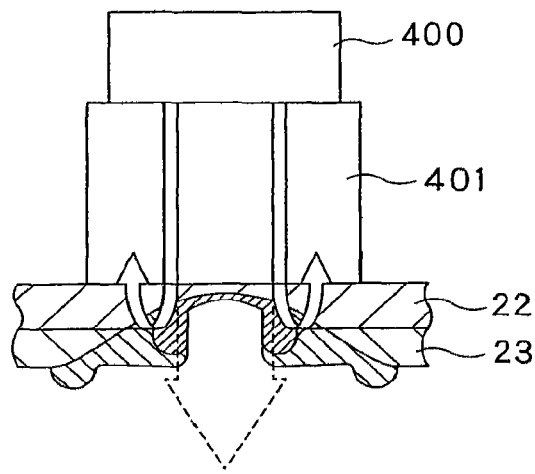
FIG. 23 is a diagram for illustrating a measuring method employing an ultrasonic probe 400, this method being a sixth embodiment of the present invention.
Figure 24:
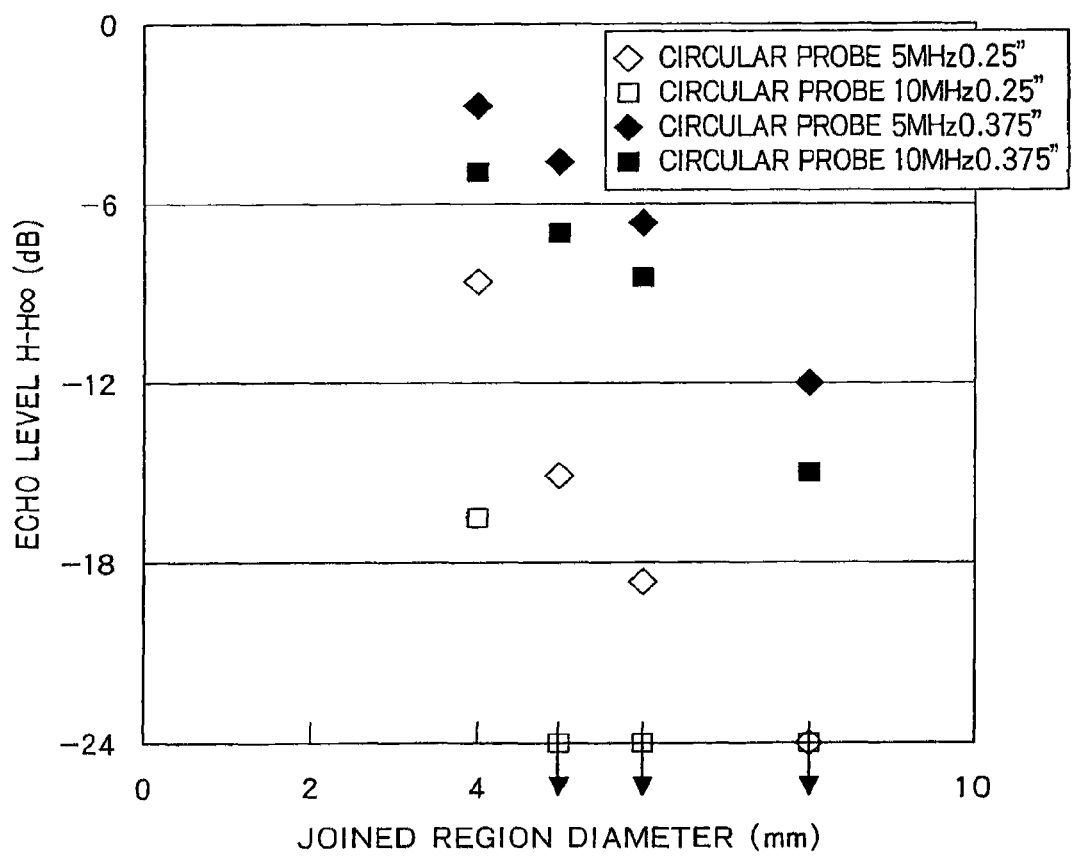
FIG. 24 is a graph showing a relationship between a joined region diameter and the echo level, in the measuring method according to the sixth embodiment of the present invention.
Figure 25:
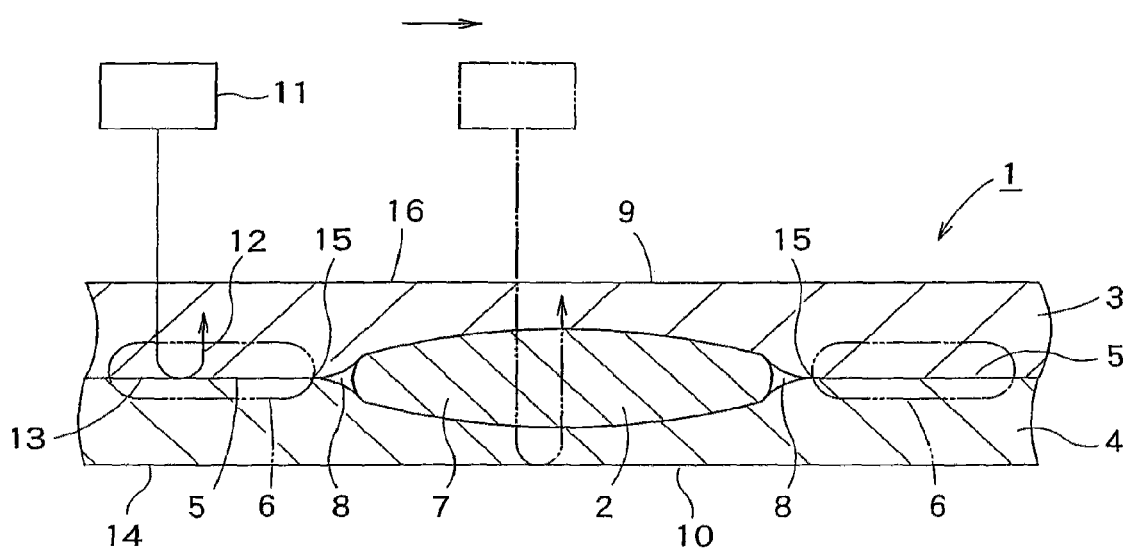
FIG. 25 is a diagram for illustrating the estimation method for estimating the welded region 2 of the welded object 1 welded by the resistance spot welding of the conventional art.

FIG. 23 is a diagram for illustrating a measuring method employing the ultrasonic probe 400 composed of a vertical oscillator, the method being a sixth embodiment of the present invention. FIG. 24 is a graph showing a relationship between a joined region diameter and the echo level in the measuring method according to the sixth embodiment of the present invention.

In this embodiment, an ultrasonic beam having a cross section greater than the joined region diameter is introduced into the joining member 22 by using the ultrasonic probe 400 composed of the vertical oscillator while the reflected wave of the ultrasonic wave introduced into the joining member 22 is taken in the ultrasonic probe 400 (Reflected wave measuring step). The ultrasonic beam radiated from the ultrasonic probe 400 is introduced into the joining member 22 through an ultrasonic propagator 401 located between the ultrasonic probe 400 and the joining member 22.

In this embodiment, the joining strength of the joined object 20 is estimated based on the reflected echo level obtained by the reflected wave measuring step (Strength estimation step). Namely, by measuring in advance the relationship between the joined region diameter of the joined object and the echo level as shown in FIG. 24, the joined region diameter can be estimated by measuring the echo level even in the case of the joined object 20 having an unknown joined region diameter.

In this way, according to the above embodiment, the joining strength can be directly estimated without estimating the area of the joined region, and the joining strength of the joined object 20 can be estimated with a simple and low-cost method.

It is contemplated that the testing method and the testing apparatus employing the estimation method of the first embodiment are included in the present invention, and that the testing methods and the testing apparatuses employing the estimation methods of the second to sixth embodiments are also included in the present invention. Namely, also in the second to sixth embodiments, the quality of the joined object can be inspected, without destroying the joined object, by judging whether or not the joined object can satisfy a predetermined quality, based on an obtained estimation result.

In addition, a case of displaying the estimation result obtained by estimating the joined region 21, by using the display 40, without estimating the joining strength, is also included in the above embodiment. Furthermore, an inspector may judge the joining quality including the joining strength or the like, by displaying an image showing the shape of the joined region 21 on a two-dimensional plane. While, in the above embodiment, the estimation apparatus 30, 130 performs the estimation of the joining region 21 and/or the joining strength, the estimation method is not limited to this aspect. For instance, an estimation method in which a person conducts the aforementioned steps is also within the scope of this invention. While the joined region 21 is estimated in the above embodiment, the stir-joined region 21c and the pressure-joined region 21d may be estimated, instead, individually, in the same procedure. While, in the above embodiment, the upper plate 22 and the lower plate 23 are respectively formed from an aluminum alloy, the joined object 20 may be formed from any other suitable materials, provided that these materials can be joined by the friction stir joining method. In addition, as the ultrasonic probe, a general purpose device may be used.

As stated above, while preferred examples of this invention have been shown and described specifically to some extent, it is obvious that various modifications can be made thereto. Accordingly, it should be understood that the present invention can be implemented in various aspects different from those specifically shown and described herein without departing from the scope and spirit of the claimed invention.

The invention claimed is:

1. A method of estimating a joining strength of a joined object in which two joining members are joined together while being overlapped one on another by using a spot friction stir joining method, comprising:
   introducing an ultrasonic beam, by using a vertical oscillator, into a joined region of the joined object from a face of the joined object opposed to a plunging face thereof in which a joining tool was plunged during a friction stir process, the beam having a cross section at a surface of the joined object that is larger than a diameter of the joined region at the plunging face;
   taking in a reflected wave of the ultrasonic beam introduced into and reflected from the joined object; and
   estimating the joining strength of the joined object, based on a reflected echo level obtained by measuring the reflected wave.

2. A method of testing a joined object in which two joining members are joined together while being overlapped one on another by using a friction stir joining method, the testing method comprising the step of inspecting the joined object based on an estimation result obtained by the estimation method according to claim 1.

3. A method of estimating a joint strength, the method comprising:
   providing a joined object having two overlapping members that are joined together in a mutually overlapping region by using spot friction stir joining, where a joining tool forms a joined a joined region at a plunging face of the joined object;
   introducing an ultrasonic beam from a vertical oscillator into the joined region from a face of the joined object opposite the plunging face, the beam having a cross section dimension that is greater than all dimensions of the joined region;
   measuring a reflected echo level of a reflected wave of the ultrasonic beam; and
   estimating the joint strength of the joined object based on the reflected echo level.

4. The method of estimating a joint strength according to claim 3, wherein
   for purposes of comparison with the dimensions of the joined region, the beam is measured at a surface of the joined object.

* * * * *